(12) United States Patent
Schwartz

(10) Patent No.: US 12,097,134 B2
(45) Date of Patent: Sep. 24, 2024

(54) ABSORBABLE INTRAVASCULAR DEVICES THAT PROVIDE A DECREASE IN RADIAL RIGIDITY OF THE VESSEL OVER TIME

(71) Applicant: EFEMORAL MEDICAL, INC., Los Altos, CA (US)

(72) Inventor: Lewis B. Schwartz, Lake Forest, IL (US)

(73) Assignee: EFEMORAL MEDICAL, INC., Los Altos, CA (US)

( * ) Notice: Subject to any disclaimer, the term of this patent is extended or adjusted under 35 U.S.C. 154(b) by 1010 days.

(21) Appl. No.: 17/003,826

(22) Filed: Aug. 26, 2020

(65) Prior Publication Data

US 2020/0390569 A1 Dec. 17, 2020

Related U.S. Application Data

(63) Continuation-in-part of application No. 16/159,508, filed on Oct. 12, 2018, now Pat. No. 10,828,184.

(60) Provisional application No. 62/571,813, filed on Oct. 13, 2017.

(51) Int. Cl.
*A61F 2/82* (2013.01)
*A61F 2/958* (2013.01)

(52) U.S. Cl.
CPC ................ *A61F 2/82* (2013.01); *A61F 2/958* (2013.01); *A61F 2002/825* (2013.01); *A61F 2250/0036* (2013.01)

(58) Field of Classification Search
CPC ........ A61F 2/07; A61F 2/2412; A61F 2/2442; A61F 2/82; A61F 2/958; A61F 2250/0036; A61F 2002/825
See application file for complete search history.

(56) References Cited

U.S. PATENT DOCUMENTS

| | | |
|---|---|---|
| 2010/0042202 A1 | 2/2010 | Ramzipoor et al. |
| 2010/0125328 A1 | 5/2010 | Flanagan |
| 2014/0114430 A1* | 4/2014 | Pasini ..................... A61F 2/915 703/1 |
| 2016/0262915 A1* | 9/2016 | Mangiardi ............... A61F 2/90 |
| 2017/0281832 A1 | 10/2017 | Ramzipoor et al. |

FOREIGN PATENT DOCUMENTS

| | | |
|---|---|---|
| WO | 2016141215 A1 | 9/2016 |
| WO | 2018067171 A1 | 4/2018 |

* cited by examiner

*Primary Examiner* — Jason-Dennis N Stewart
(74) *Attorney, Agent, or Firm* — Convergence Intellectual Property Law P.C.; Jonathan Garfinkel

(57) ABSTRACT

A vascular stent may be used to maintain or enhance patency of a blood vessel. By using multiple, separate stent elements that are balloon expandable, the multi-element stent may be stronger than a traditional self-expanding stent but may also be more flexible, due to its multiple-element configuration, than a traditional balloon-expandable stent. The stent elements are formed from a bioresorbable polymer material. The radial rigidity of the stent is configured to decrease after implantation in a vessel as the polymer is absorbed. The thickness of the stent, cell shape, polymer material, and/or treatment of the polymer material may be configured to provide a high initial radial rigidity to the vessel upon implantation and a decrease in the radial rigidity of the vessel over time.

5 Claims, 21 Drawing Sheets

ABSORBABLE INTRAVASCULAR DEVICES THAT PROVIDE A DECREASE IN RADIAL RIGIDITY OF THE VESSEL OVER TIME

CROSS-REFERENCES TO RELATED APPLICATIONS

This application is a continuation-in-part of U.S. patent application Ser. No. 16/159,508, entitled "ABSORBABLE INTRAVASCULAR DEVICES THAT PROVIDE A DECREASE IN RADIAL RIGIDITY OF THE VESSEL OVER TIME", filed on Oct. 12, 2018, which claims the benefit and priority of U.S. Provisional Patent Application No. 62/571,813, entitled "ABSORBABLE INTRAVASCULAR DEVICES THAT PROVIDE A DECREASE IN RADIAL RIGIDITY OF THE VESSEL OVER TIME", filed on Oct. 13, 2017, the full disclosures of the above referenced applications are incorporated herein by reference.

FIELD OF THE INVENTION

The present application pertains generally to the field of medical devices. More specifically, the present application pertains to the design and manufacture of intravascular stents intended to maintain patency (blood flow) of blood vessels (arteries and veins).

BACKGROUND

Atherosclerotic cardiovascular disease or "hardening of the arteries" is the leading cause of death and disability in the world accounting for nearly one-third of all human mortality. Although some developed nations have made significant strides in modifying risk factors and changing lifestyle behaviors, the global prevalence of atherosclerotic disease is still rising with some projections predicting >23 million annual deaths by the year 2030. The economic burden is staggering; in the United States alone, the estimated yearly cost treating atherosclerosis and its sequelae exceeds $200 billion.

Atherosclerosis is a process of pathological arterial aging. In youth, supple elastin fibers within the arterial media provide the structural elasticity and compliance required for arterial pulsation and pulse wave transmission. Over decades, however, the persistent pressure and motion slowly denatures structural matrix proteins causing elastin fatigue and fracture. The result is a slow but inexorable loss of distensibility; the arterial wall chronically stiffens. With the loss of pulsatility and wave reflection, the flow velocity profile becomes blunted; flow reversal is lost and the modulus of antegrade flow is attenuated. This creates long periods of relative stasis in diastole and increasing particle and cellular residence time at the wall. The dysfunctional wall beneath the stagnant boundary layer begins to accumulate circulating atherogenic cholesteryl fatty acyl esters and triglycerides particles, particularly apolipoprotein B-containing lipoproteins. Oxidative modification of the lipoproteins activates the overlying endothelium to secrete chemokines which attract blood-borne monocytes rolling along the endothelium to tether to the vascular surface made sticky by exposure of adhesion molecules and tissue factor. Diapedesis of firmly attached monocytes traps the cells within the thickened subendothelial space. Thus initiated, the ongoing pathological process generates fatty, occlusive lesions via cholesterol-loaded foam cells, continued recruitment and infiltration of inflammatory and hematopoietic cells, and a progressive accumulation of lipid matrix and smooth muscle proliferation that slowly begins to raise the endothelium and encroach upon the arterial lumen. When grown large enough to reduce the flow of blood and oxygen to vital organs, atherosclerotic plaques produce the chronic clinical syndromes of chest pain (angina pectoris), mini-stroke (transient ischemic attack) and poor circulation (claudication). More complex plaques with ossified cores and degenerating fibrous caps can abruptly rupture leading to acute occlusion of the arteries in which they reside. These generate the critical, life-threatening clinical events of heart attack (myocardial infarction), stroke (cerebrovascular accident) and gangrene (critical limb ischemia).

Intravascular Metal Stents

The first stent type to be widely applied to the treatment of atherosclerotic plaques was a balloon-expandable stents (BES) designed as an open mesh tube comprised of stainless steel. When crimped onto an angioplasty balloon it could be advanced through the arterial tree coaxially and deployed directly within the plaque. Stent implantation created a larger and more durable flow channel as compared to balloon angioplasty alone.

In the modern era, balloon-expandable stents are deployed in virtually every case of percutaneous coronary intervention (PCI) and in about half of all peripheral interventional procedures.

In order to prop open large arteries and avoid excessive recoil and deformation, peripheral BES are rigid medical devices. They are typically designed to withstand pressures of $0.5-2\times10^5$ Pa (375-1500 mmHg, 0.05-0.2 N/mm$^2$), non-physiologic forces that far exceed any intra- or extravascular pressure observed within the human body. In fact, BES are more than ten times rigid than the vessels they occupy. Because they are so rigid, BES can only be implanted in a limited number of anatomic locations, namely those with minimal or highly predictable arterial motion such as the coronary, renal and common iliac arteries. As such, implantation of BES are absolutely contraindicated in a number of important peripheral vascular beds including the carotid, subclavian, external iliac, common femoral, superficial femoral and popliteal arteries.

The rigidity of BES also severely limits their usable length. Implanted stents that are too long will kink or tear arteries in motion leading to restenosis, thrombosis, pseudoaneurysm formation and, in some cases, device fracture and migration. Knowing their dangers, stent manufacturers make their devices available in limited lengths. Although atherosclerotic lesions in peripheral arteries can be several hundred mm long, the longest available BES is only 60 mm. They are clearly inadequate for intervention in the leg where lesions >200 mm are routinely encountered.

As early as 1969, it was theorized that intravascular stents should be flexible rather than rigid. First developed for aerospace applications, an equiatomic alloy made of nickel-titanium called nitinol was thought to exemplify the ideal mechanical properties for the scaffolding of blood vessels. One property was superelasticity, or the ability of a metal to return to its original shape after a substantial deformation. This assured flexibility within arteries in motion within the human body. The other property was shape memory, or the ability of an alloy to be annealed at one temperature, substantially deformed at a lower temperature, then returned to its original shape when heated. This allowed nitinol stents to be compressed into their delivery systems at low temperatures, then released and expanded within the warm mammalian environment at the time of implantation.

The first self-expanding nitinol stent (SES) to be approved for clinical use was a simple, coiled wire made of nitinol. It was introduced into the American market in 1992. Seamless tubes of nitinol became available shortly thereafter, enabling the development of laser-cut, tubular nitinol stents. In the modern era, tubular, nitinol SES are the most common devices deployed in long, flexible blood vessels such as the external iliac and superficial femoral arteries.

Because SES generate much less force than BES, they expand vessels much less completely. In order to get them to expand more fully, SES are routinely post-dilated with high-diameter balloons following their deployment. Even after repeated balloon dilatation, however, the relatively weak SES cannot overcome the inward force of the recoiling artery resulting in an insufficient post-procedure diameter. This is a surprisingly frequent occurrence after SES deployment, especially in peripheral arteries burdened with significant atherosclerosis disease. In one study, underexpansion of the target lesion (≥30% residual stenosis) was observed in 70% of cases after SES implantation into calcific arteries.

The second drawback of the use of nitinol SES is their disquieting tendency toward fracture. Only occasionally observed with BES, SES fracture is alarmingly common, as high as 65% in one clinical report. Although not fully understood, one attractive hypothesis for this phenomenon is that fracture may be a function of the unique biomechanical forces exerted on stents dwelling in the lower extremities. Movement of the legs is a complex motion; loading of the hips and knees during ambulation repeatedly compresses the arteries axially and can even produce multidimensional bends, twists and kinks. The result is single or multiple strut fractures or, in severe cases, complete stent transection. Fracture is more common after implantation of long and/or overlapping stents and, possibly, in more active patients. Fracture of intravascular stents is clearly associated with restenosis, although it remains controversial whether the relationship is associative or causal.

The unique mechanism and design of SES assures that the pattern of chronic forces exerted upon the stented artery are far different than for BES. After deployment of BES, the forces exerted upon the artery are static and temporary. The artery is perturbed by the initial stretch and stent deployment but, once recovered, heals completely and returns to quiescence. Vessels that house a nitinol SES, however, are continually subjected to the chronic outward forces (COF) exerted by the ever-expanding and twisting device. A COF accompanies all SES implantations because, by definition, SES must be "oversized" when implanted. That is to say that the nominal diameter of the stent must, in all cases, exceed the target lesion's reference vessel diameter (RVD) so that the flexible and non-anchored device will remain in place following deployment. Because the final diameter of the device is always less than its nominal "shape memory" diameter when manufactured, it will continue to exert an outward expansive force upon the wall of the vessel until such time that its nominal diameter is reached (if ever). Combined with the motion of the vessels in which SES are typically implanted, this assures a continual and chronic perturbation of the vessel wall for many years following device deployment. The artery responds with chronic inflammation, foreign body reaction, smooth muscle cell proliferation and restenosis. This is particularly troublesome in anatomic areas prone to bending and twisting, such as the common femoral artery. The problem is so prevalent that implantation of nitinol SES at the hip or knee is surgically contraindicated.

Lastly, although nitinol SES are far more flexible than their BES counterparts, continued thickening of arteries treated with SES assures that the stented artery will eventually be rendered more rigid. Even arteries treated with so-called "flexible" stents will generate a significant foreign body response, stiffen, and induce kinking and twisting of the unstented segments. Exaggerated movement of the remaining artery may still allow limited movement and preserve patency, but the resultant aberrant flow patterns and conformations too often lead to thrombosis and failure.

Given the non-physiologic nature of SES in the high-resistance peripheral vasculature, their poor overall effectiveness is not surprising. The one-year primary patency of superficial femoral arteries treated with SES remains a dismal 60% and continues to decline with each successive year.

Absorbable Intravascular Stents

To address the myriad problems associated with permanent metal implants, stents that slowly dissolve after deployment have long been imagined. So-called "bioresorbable vascular scaffolds" (BVS) potentially offer several key biologic and physiologic advantages including, (1) effective scaffolding without the permanence of a metal implant, (2) attenuation of inflammation and chronic foreign body reaction leading to reduced restenosis and enhanced long-term patency, (3) assistance of adaptive vascular remodeling, (4) restoration of physiologic vasoactive function, and (5) facilitation of imaging and surveillance during follow-up.

The original bioresorbable device was the "catgut" surgical suture, first evident in the historical record some four millennia ago. Catgut sutures are derived from dried sheep, goat or bovine intestine, but have retained the name "catgut" probably because they were also used as strings for musical instruments sometimes referred to as "kits". Catgut sutures are enzymatically degraded and resorbed in vivo so can be classified as bioresorbable. More contemporary bioresorbable surgical sutures are synthetic. Other, more recently developed bioresorbable medical devices includes bioresorbable screws and fracture plates for the treatment of traumatic injuries, indwelling scaffolds that serve as a basis for tissue engineering and regenerative medicine, chemotherapy-loaded polymers for therapeutic oncology, inert synthetic wraps for the prevention of post-operative peritoneal adhesions, bioabsorbable scaffolds for stenting of the upper airways and Eustachian tubes, and bioresorbable intravascular scaffolds (stents). Unfortunately, recent, more longer-term results have raised questions regarding the safety and efficacy of the first-generation absorbable coronary stent.

Therefore, it would be advantageous to have a stent for use in vasculature that is rigid upon implantation so as to aximally dilate and scaffold the artery, but then slowly decreases in rigidity to allow the blood vessel to return to its original, healthy, flexible state. At least some of these objectives will be met by the embodiments described below.

SUMMARY

The embodiments herein describe a device for placement within a blood vessel to maintain or enhance blood flow through the blood vessel. The device may comprise multiple, balloon-expandable, bioresorbable, vascular stent elements configured to be implanted in the blood vessel as a multi-element stent. The stent elements may be spaced such that the stent elements do not touch one another. The stent elements are formed from a bioresorbable polymer material. The radial rigidity of the stent is configured to decrease after implantation in a vessel as the polymer is absorbed. In some embodiments, the stent is configured to provide an initial radial rigidity to the vessel upon implantation of approximately 15 N/cm or more. The stent may be configured to provide a decrease in the radial rigidity of the vessel over a period of approximately 2 years to a radial rigidity of less than 1 N/cm. The thickness of the stent, cell shape, polymer material, and treatment of the polymer material may be configured to provide the decrease in radial rigidity of the vessel over time.

In some embodiments, the stent may be formed from a material comprising poly(L-lactic acid) (PLLA), poly(D-lactic acid) (PDLA), poly(D,L-lactic acid) (PDLLA), semicrystalline polylactide, polyglycolic acid (PGA), poly(lactic-co-glycolic acid) (PLGA), poly(iodinated desamino tyrosyl-tyrosine ethyl ester) carbonate, polycaprolactone (PCL), salicylate based polymer, polydioxanone (PDS), poly(hydroxybutyrate), poly(hydroxybutyrate-co-valerate), polyorthoester, polyanhydride, poly(glycolic acid-co-trimethylene carbonate), poly(iodinated desaminotyrosyl-tyrosine ethyl ester) carbonate, polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, polyurethane including polycarbonate urethanes, polyethylene, polyethylene terephthalate, ethylene vinyl acetate, ethylene vinyl alcohol, silicone including polysiloxanes and substituted polysiloxanes, polyethylene oxide, polybutylene terephthalate-co-PEG, PCL-co-PEG, PLA-co-PEG, PLLA-co-PCL, polyacrylates, polyvinyl pyrrolidone, polyacrylamide, or combinations thereof.

In an embodiment, the stent comprises a therapeutic drug. The therapeutic drug may prevent or attenuate inflammation, cell dysfunction, cell activation, cell proliferation, neointimal formation, thickening, late atherosclerotic change or thrombosis.

In an embodiment, the radial rigidity of the stent is slowly attenuated as its structural polymer is unlinked and metabolized such that the stent slowly becomes more flexible causing adaptation and remodeling of the vessel and restoration of the vessel's elasticity.

This and other aspects of the present disclosure are described herein.

BRIEF DESCRIPTION OF THE DRAWINGS

Present embodiments have other advantages and features which will be more readily apparent from the following detailed description and the appended claims, when taken in conjunction with the accompanying drawings, in which:

FIG. 5A is a two-dimensional depiction of an element. FIGS. 5B, 5D, and 5E are magnified views of the cells in FIG. 5A. FIGS. 5C and 5F show the stent element of FIG. 5A in cylindrical form.

DETAILED DESCRIPTION

Figure 1:
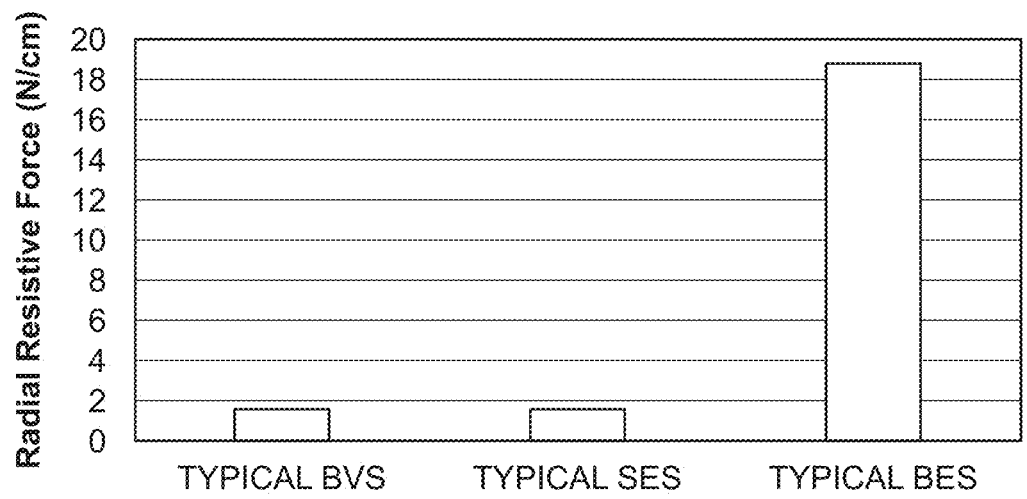
FIG. 1 shows the typical radial resistive forces of intravascular stents.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

Various embodiments are described herein with reference to the figures. The figures are not drawn to scale and are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 shows the typical radial resistive forces of intravascular stents. A typical "bioresorbable vascular scaffold" (BVS) or absorbable stent has a radial resistive force of under 2 N/cm. Similarly, a typical self-expanding metal stent (SES) has a radial resistive force of under 2 N/cm. Typical balloon-expandable metal stents (BES) have a much higher radial resistive force, sometimes above 18 N/cm.

The embodiments herein describe the design of a new, intravascular absorbable device that maintains the flow channel (patency) of long blood vessels by providing temporary, rigid, radial support that is far greater than that provided by a typical absorbable or metal self-expanding stent (SES) and commensurate with that provided by a metal balloon-expandable stent (BES). Once implanted, the absorbable device imparts a high degree of radial force to prop open the diseased artery; the force is roughly equivalent to a large diameter, peripheral, balloon-expandable metal stent.

In contrast to most stent patterns which are designed to marry both radial force and longitudinal flexibility, the patterns described herein are specifically tailored to maximize radial force and rigidity and forego longitudinal and axial flexibility.

The devices described herein are multi-element, vascular stents (or "vascular scaffolds"). These stents are comprised of multiple, short, rigid, cylindrical stent segments, or elements, which are separate from one another but may be referred to together as a multi-element stent.

Generally, each element of the multi-element stents described herein will be sufficiently rigid to provide a desired level of strength to withstand the stresses of the vessel in which they are placed, such as a tortuous peripheral vessel. At the same time, a multi element stent will also be flexible, due to the fact that it is made up of multiple separate elements, thus allowing for placement within a curved, torturous blood vessel.

Additionally, the multi element stents described herein will usually be balloon-expandable rather than self-expanding, since balloon-expandable stents are typically stronger than self-expanding stents. Each balloon expandable element of the stent may have relatively high radial force (rigidity) due to the described structures and materials. A stent element is defined as being radially rigid if it has a radial strength significantly higher than self-expanding stents that is similar or greater in magnitude to that of traditional, metal balloon-expandable stents, such as those made of steel or cobalt-chromium.

When mounted serially on an inflatable balloon, they can be simultaneously implanted side-by-side in long blood vessels. During motion of the organism, the elements can move independently, maintaining their individual shape and strength while the intervening, non-stented elements of the vessel can twist, bend and rotate unencumbered. The result is a treated vessel with a rigidly maintained flow channel that still enjoys unrestricted flexibility during organismal movement.

The described embodiments exploit the principles that, (1) a rigid device that is deployed via balloon-expansion represents the optimal design of an intravascular stent given its transient effect on the arterial wall and relative ease of precise implantation, (2) a long, rigid device cannot be safely implanted in an artery that bends and twists with skeletal motion, (3) long arteries that bend and twist could be effectively treated with multiple, short BES that allow the intervening, non-stented arterial elements to move unencumbered, (4) the length, number and spacing of the stent elements could be determined by the known and predictable bending characteristics of the target arteries, and (5) arteries need only be scaffolded transiently; late dissolution of the stent will have little effect on the long-term effectiveness of treatment.

Indicated for the treatment of long, occlusive lesions in bendable human arteries such as the superficial femoral artery of the thigh, the device may be fashioned as a series of identical or near-identical rigid elements that are evenly spaced on a single, long balloon. Spacing of elements in multi-element stents has been described in PCT International Application Number PCT/US16/55953, entitled "RADIALLY RIGID AND LONGITUDINALLY FLEXIBLE MULTI-ELEMENT INTRAVASCULAR. STENT", the full disclosure of which is herein incorporated by reference.

Figure 2A:
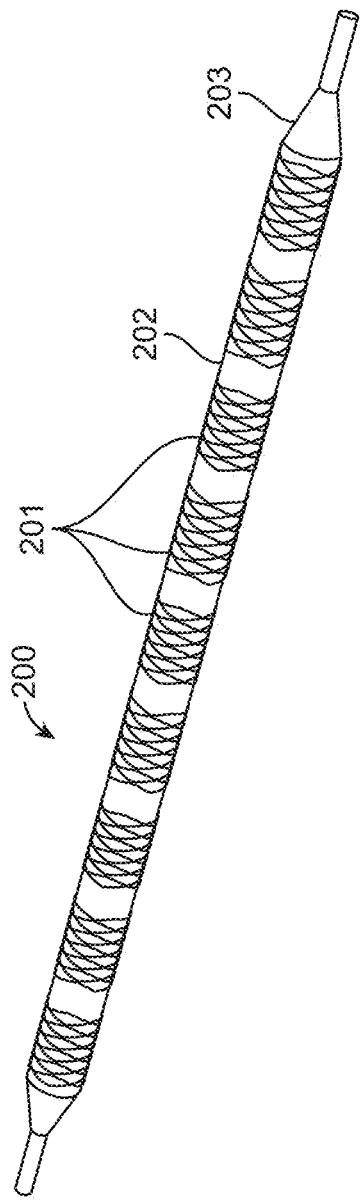
FIG. 2A illustrates one embodiment of a multi-element stent.
Figure 2B:
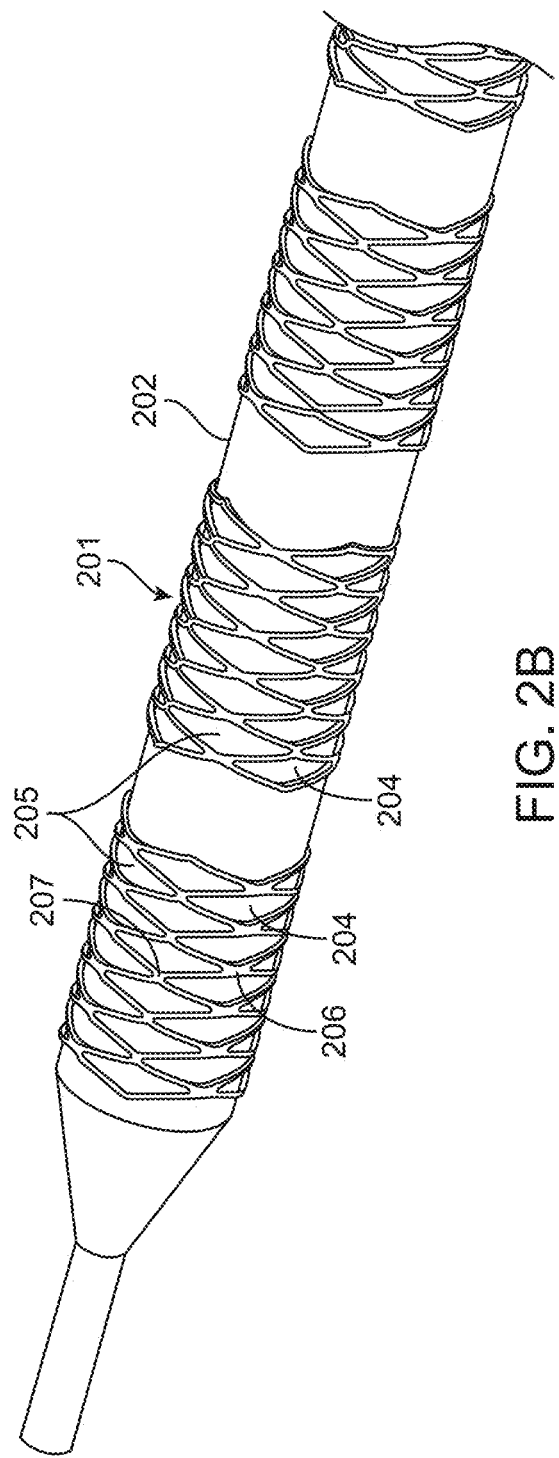
FIG. 2B is a magnified view of the stent elements in FIG. 2A.

One embodiment of the fully assembled device in shown in FIG. 2A. A single balloon inflation and device deployment can treat a long segment of diseased artery while still preserving the critical ability of the artery to bend with skeletal motion such as sitting or walking. Multi-element stent 200 comprises multiple stent elements 201. Individual balloon-expandable stent elements 201 are crimped onto an inflatable balloon 203 to facilitate delivery. FIG. 2B is a magnified view of the stent elements 201 in FIG. 2A. Individual elements 201 are positioned serially along a longitudinal length of the balloon 203 and spaced such that the stent elements 201 do not touch one another. Further, the spacing is such that after deployment, the stent elements 201 do not touch or overlap during skeletal movement. The number of elements 201, length of elements, and gap 202 between elements 201 may vary depending on the target vessel location. In an embodiment, each element 201 in the multi-element stent 200 has the same length. In multi-element stents having three or more elements 201, and thus two or more gaps 202, the gaps may be of the same length.

Figure 3A:
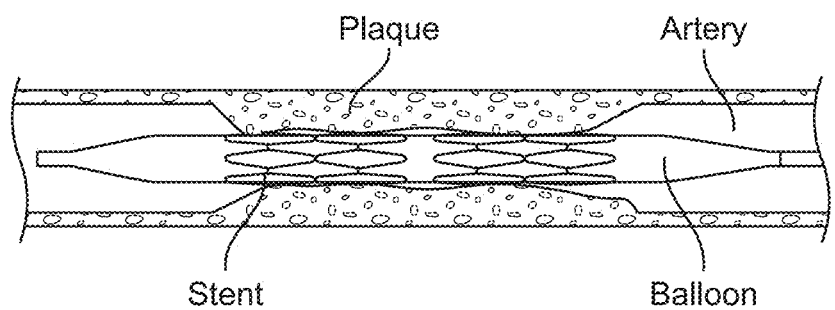
FIGS. 3A-3C depict deployment of a balloon-expandable multi-element stent.
Figure 3B:
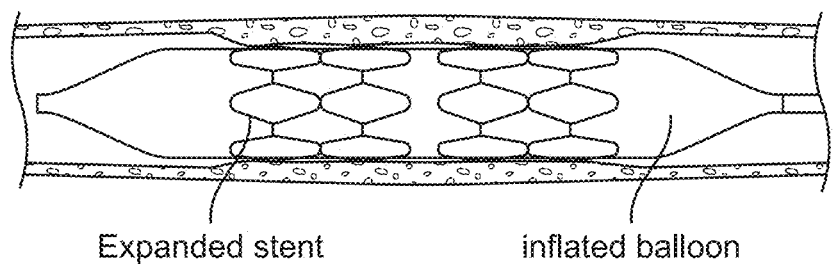
Figure 3C:
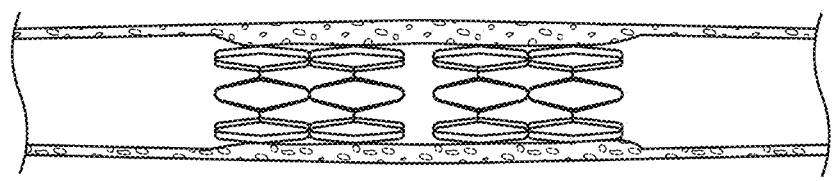

FIGS. 3A-3C depict deployment of a balloon-expandable multi-element stent. In FIG. 3A a multi-element stent mounted on a balloon is advanced to the lesion. In FIG. 3B the balloon and stent are expanded. In FIG. 3C the balloon is withdrawn leaving the multi-element stent still within the artery.

Figure 4A:
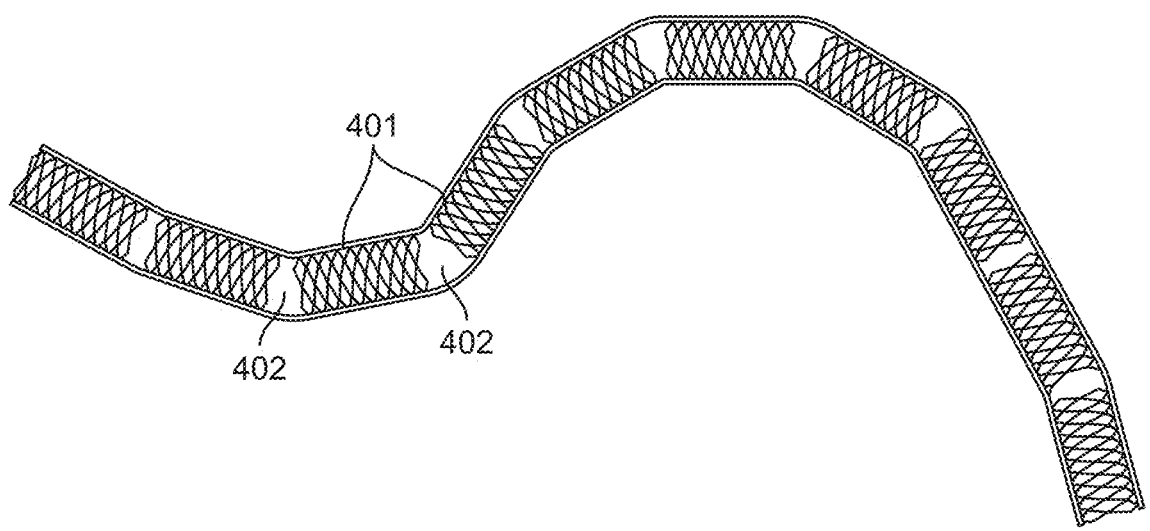
FIG. 4A shows an implanted multi-element stent in a popliteal artery during full flexion of the hip and knee.
Figure 4B:
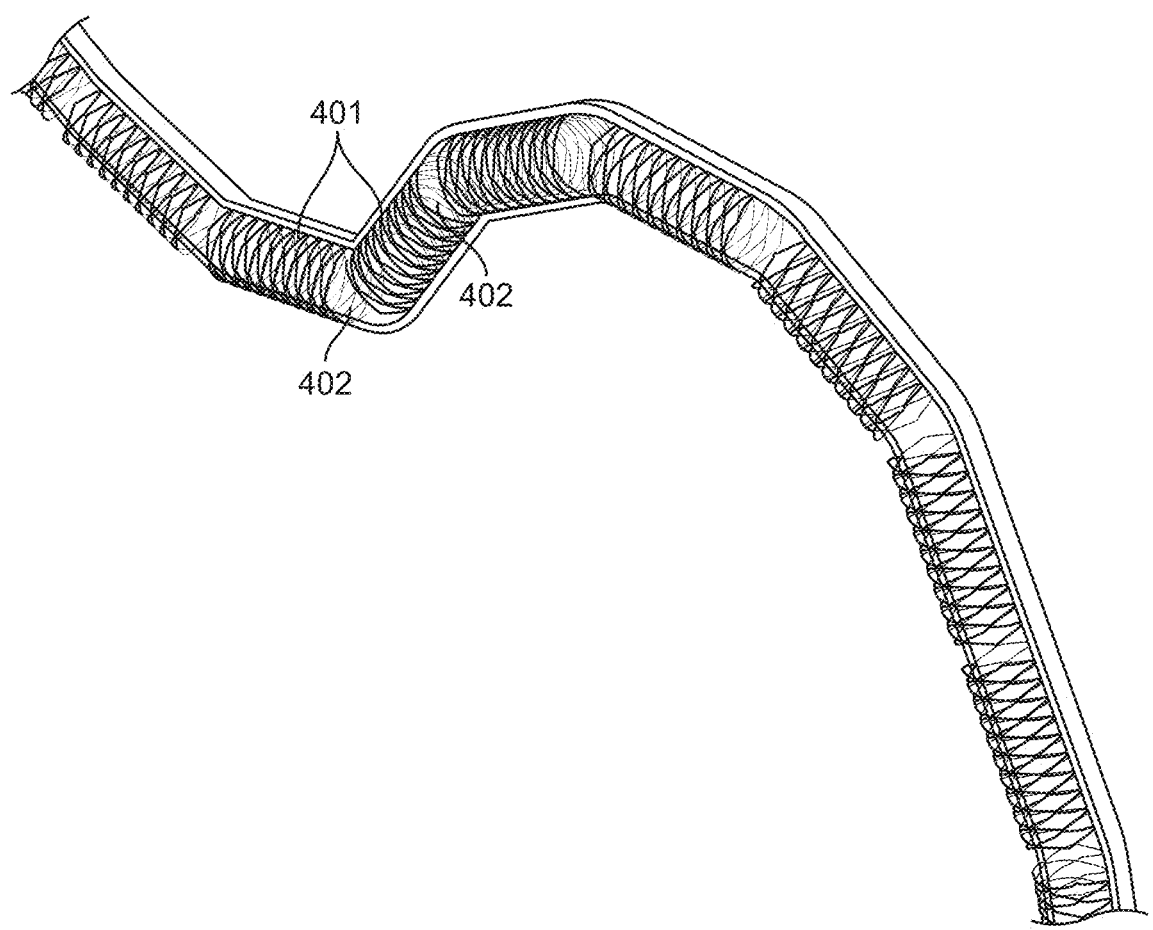
FIG. 4B depicts the implanted device of FIG. 4A shown in three dimensions.
Figure 5C:
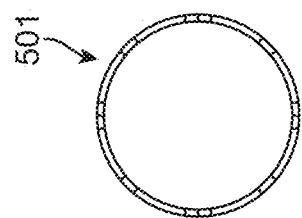
FIGS. 5A-5F show an embodiment of a stent pattern.
Figure 5B:
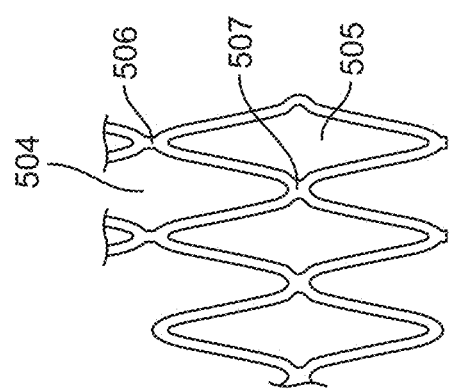
Figure 5E:
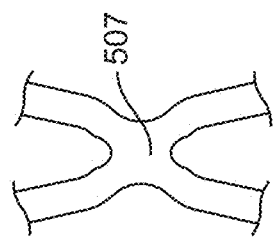
Figure 5D:
Figure 5A:
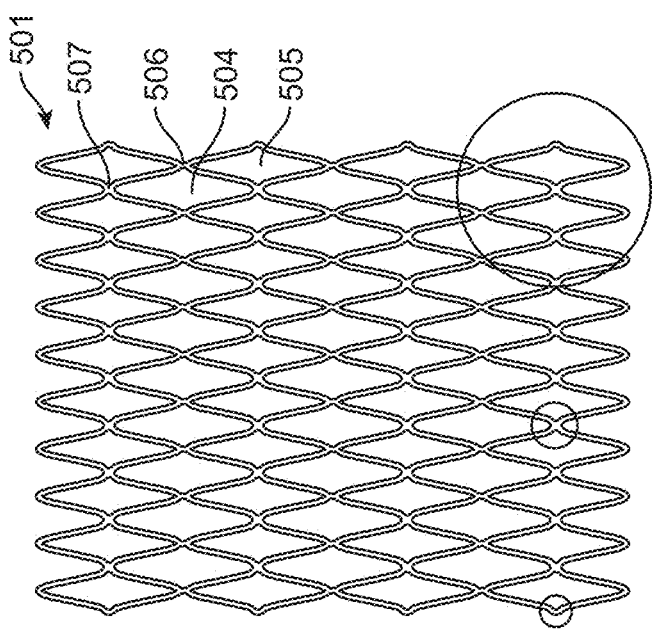
Figure 5F:
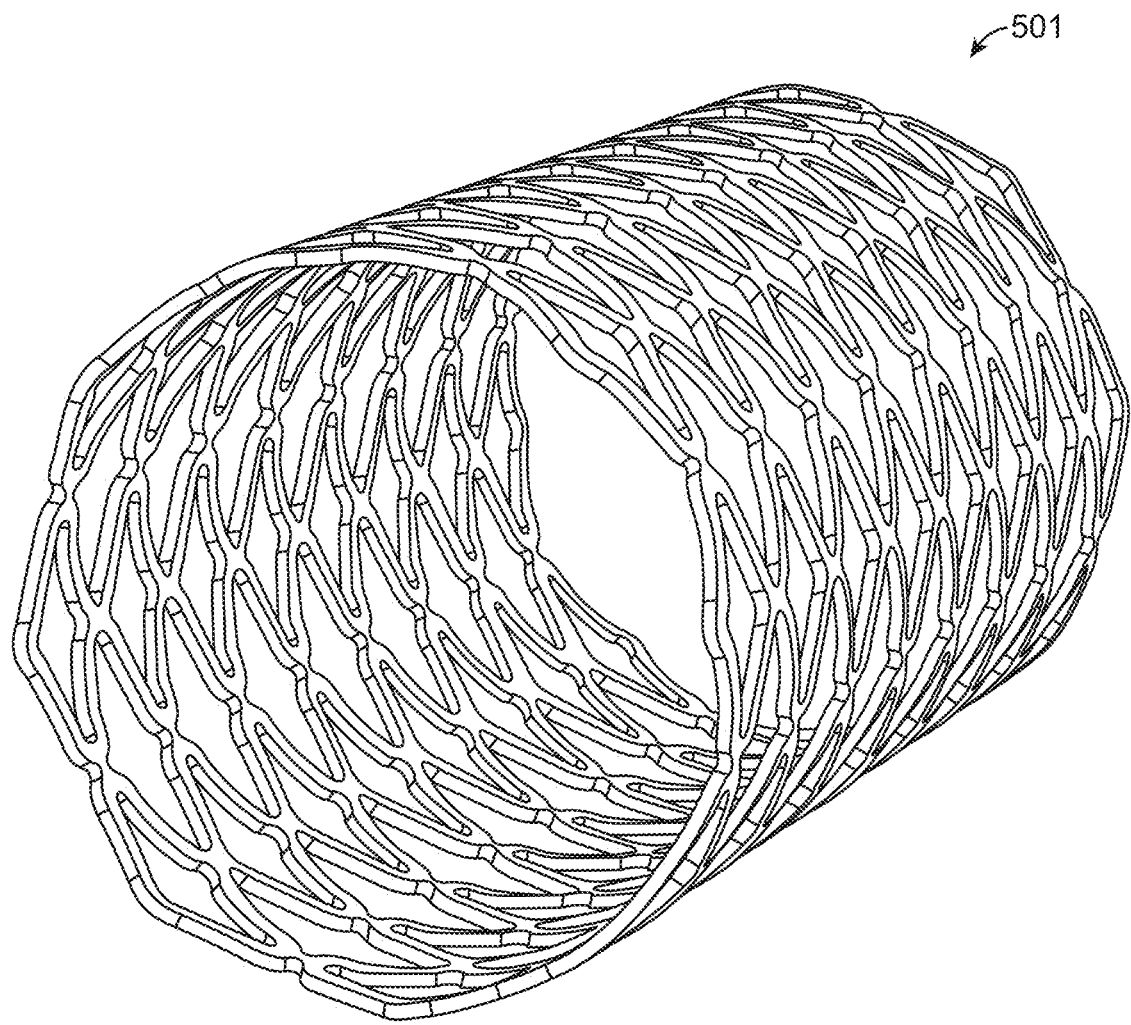

FIG. 4A shows an implanted multi-element stent in a popliteal artery during full flexion of the hip and knee. FIG. 4B depicts the implanted device of FIG. 4A shown in three dimensions. The individual stent elements 401 are spaced such that they do not overlap even when the artery is highly bent. Unencumbered arterial movement is afforded through flexion or extension of the unstented gaps 402.

The stents described herein may be formed from various different materials. In an embodiment, stents may be formed a polymer. In various alternative embodiments, the stent or stent element may be made from any suitable bioresorbable material such that it will dissolve non-toxically in the human body, such as but not limited to poly(L-lactic acid) (PLLA), polyglycolic acid (PGA), poly(iodinated desaminotyrosyl-tyrosine ethyl ester) carbonate, or the like.

In alternative embodiments, any suitable polymer may be used to construct the stent. The term "polymer" is intended to include a product of a polymerization reaction inclusive of homopolymers, copolymers, terpolymers, etc., whether natural or synthetic, including random, alternating, block, graft, branched, cross-linked, blends, compositions of blends and variations thereof. The polymer may be in true solution, saturated, or suspended as particles or supersaturated in the beneficial agent. The polymer can be biocompatible, or biodegradable. For purpose of illustration and not limitation, the polymeric material may include, but is not limited to, poly(D-lactic acid) (PDLA), poly(D,L-lactic acid) (PDLLA), poly(iodinated desamino tyrosyl-tyrosine ethyl ester) carbonate, poly(lactic-co-glycolic acid) (PLGA), salicylate based polymer, semicrystalline polylactide, phosphorylcholine, polycaprolactone (PCL), poly-D,L-lactic acid, poly-L-lactic acid, poly(lactideco-glycolide), poly(hydroxybutyrate), poly(hydroxybutyrate-co-valerate), polydioxanone (PDS), polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, polyurethane including polycarbonate urethanes, polyethylene, polyethylene terephthalate, ethylene vinyl acetate, ethylene vinyl alcohol, silicone including polysiloxanes and substituted polysiloxanes, polyethylene oxide, polybutylene terephthalate-co-PEG, PCL-co-PEG, PLA-co-PEG, PLLA-co-PCL, polyacrylates, polyvinyl pyrrolidone, polyacrylamide, and combinations thereof. Non-limiting examples of other suitable polymers include thermoplastic elastomers in general, polyolefin elastomers, EPDM rubbers and polyamide elastomers, and biostable plastic material including acrylic polymers, and its derivatives, nylon, polyesters and epoxies. In some embodiments, the stent may include one or more coatings, with materials like poly(D,L-lactic acid) (PDLLA). These materials are merely examples, however, and should not be seen as limiting the scope of the invention.

Stent elements may comprise various shapes and configurations. Some or all of the stent elements may comprise closed-cell structures formed by intersecting struts. Closed-cell structures may comprise diamond, square, rectangular, parallelogrammatic, triangular, pentagonal, hexagonal, heptagonal, octagonal, clover, lobular, circular, elliptical, and/or ovoid geometries. Closed-cells may also comprise slotted shapes such as H-shaped slots, I-shaped slots, J-shaped slots, and the like. Additionally or alternatively, stent may comprise open cell structures such as spiral structures, serpentine structures, zigzags structures, etc. Strut intersections may form pointed, perpendicular, rounded, bullnosed, flat, beveled, and/or chamfered cell corners. In an embodiment, stent may comprise multiple different cells having different cell shapes, orientations, and/or sizes. Various cell structures have been described in PCT International Application Number PCT/US16/20743, entitled "MULTI-ELEMENT BIORESORBABLE INTRAVASCULAR STENT", the full disclosure of which is herein incorporated by reference. In an embodiment, stent elements may comprise a plurality of diamond shaped closed cells longer in a longitudinal direction than in a radial direction when in an unexpanded state. The stent elements may also comprise a plurality of diamond shaped closed cells longer in a radial direction than in a longitudinal direction in the expanded state.

One embodiment of a stent pattern is shown in shown in FIGS. 5A-5F. The stent elements 501 have a diamond shaped closed-cell pattern. Elements 501 comprise intermixed diamond shaped closed cells 504, 505. Diamond shaped cells 504 may be aligned in the longitudinal and/or the circumferential directions in a repeating pattern. Similarly, diamond shaped cells 505 may be aligned in the longitudinal and/or the circumferential directions in a repeating pattern. Additionally or alternatively, diamond shaped cells 504 and diamond shaped cells 505 may be helically aligned in an alternating pattern. In an embodiment, diamond shaped cells 504 and diamond shaped cells 505 are circumferentially offset. Additionally, diamond shaped cells 205 may be formed at a central location between four adjacent diamond shaped cells 504. The width and/or the height of struts 506 between two corners of longitudinally aligned diamond shaped cells 504 may be larger or smaller than the width and/or height of struts 507 between two corners of longitudinally aligned diamond shaped cells 505.

Returning to FIG. 2B, in this exemplary embodiment, the stent elements 201 have a diamond shaped closed-cell pattern. Elements 201 comprise intermixed diamond shaped closed cells 204, 205. Diamond shaped cells 204 may be aligned in the longitudinal and/or the circumferential directions in a repeating pattern. Similarly, diamond shaped cells 205 may be aligned in the longitudinal and/or the circumferential directions in a repeating pattern. Additionally or alternatively, diamond shaped cells 204 and diamond shaped cells 205 may be helically aligned in an alternating pattern. In an embodiment, diamond shaped cells 204 and diamond shaped cells 205 are circumferentially offset. Additionally, diamond shaped cells 205 may be formed at a central location between four adjacent diamond shaped cells 204. The width of struts 206 between two corners of longitudinally aligned diamond shaped cells 204 are larger than the width of struts 207 between two corners of longitudinally aligned diamond shaped cells 205.

Figure 6A:
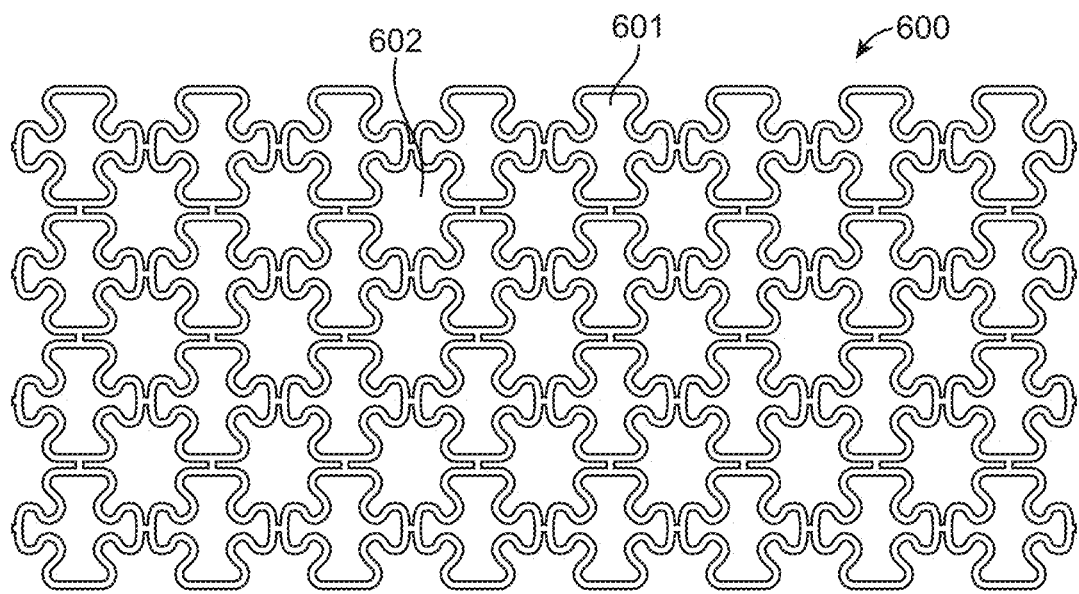
FIG. 6A is a two-dimensional depiction of an element having a lobular cell structure.
Figure 6B:
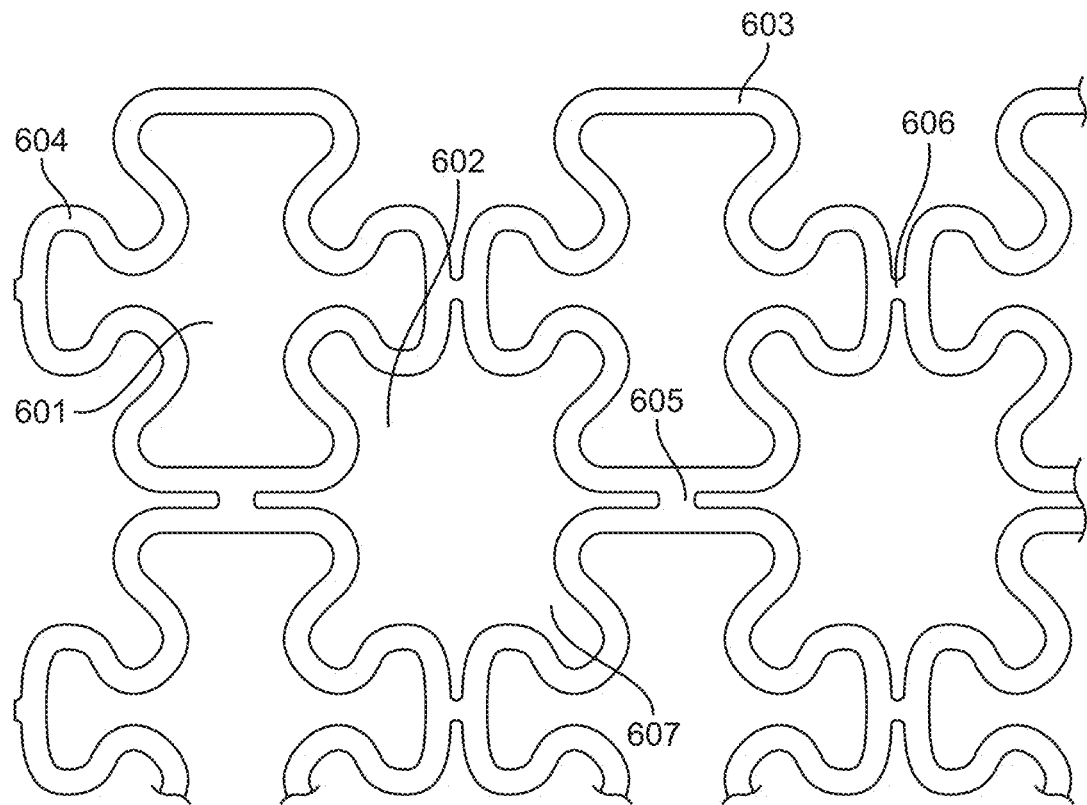
FIG. 6B is a magnified view of the cells in FIG. 6A.
Figure 6C:
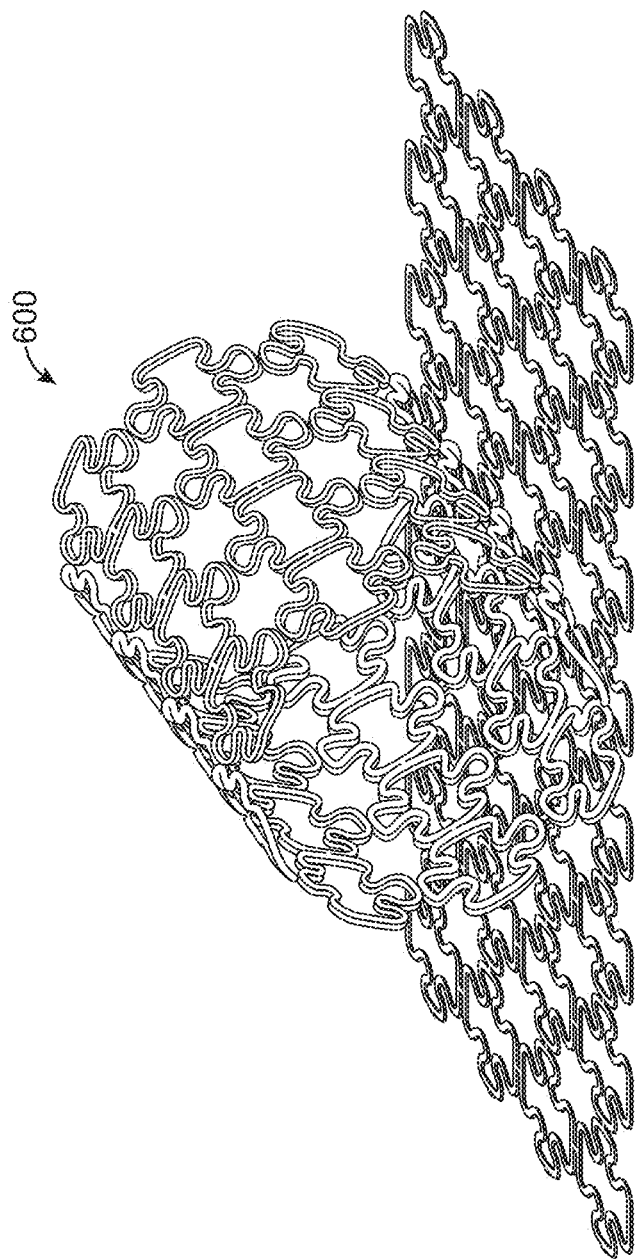
FIG. 6C shows the stent element of FIG. 6A in cylindrical form.

FIGS. 6A-6C illustrate an embodiment of a stent element having a clover or lobular cell configuration. While FIGS. 6A-6C depict cells with four lobes, cells may have any number of lobes. FIG. 6A is a two-dimensional depiction of an element having a lobular cell structure. FIG. 6B is a magnified view of the cells in FIG. 6A. FIG. 6C shows the stent element of FIG. 6A in cylindrical form wherein the two dimensional cells of FIG. 6A are wrapped from left to right to form a cylinder. In this embodiment, element 600 comprises intermixed lobular closed cells 601, 602. Lobular cells 601 may be aligned in the longitudinal and/or the circumferential directions in a repeating pattern. Similarly, lobular cells 602 may be aligned in the longitudinal and/or the circumferential directions in a repeating pattern. Additionally or alternatively, lobular cells 602 and lobular cells 601 may be helically aligned in an alternating pattern. In an embodiment, lobular cells 602 and lobular cells 601 are circumferentially offset. Additionally, lobular cells 602 may be formed at a central location between four adjacent lobular cells 601. In an embodiment illustrated in FIGS. 6A-6C, longitudinal lobes 603 aligned longitudinally are larger than circumferential lobes 604 aligned circumferentially. Alternatively, longitudinal lobes 603 may be the same size as circumferential lobes 604. Longitudinal lobes 603 of adjacent longitudinally aligned lobular cells 1001 may be connected by longitudinal connecting struts 605. Circumferential lobes 604 of adjacent circumferentially aligned lobular cells 601 may be connected by circumferential connecting struts 606. In an embodiment, longitudinal connecting struts 605 are wider than circumferential connecting struts 606. Alternatively, longitudinal connecting struts 605 may have the same widths as circumferential connecting struts 606. Element 600 may take a crimped form when mounted on an unexpanded balloon. Likewise, element 600 may take an expanded form when expanded by a balloon. Concavities 607 move away from the center of lobular element 600 as the lobular cell 601 moves from a crimped state to an expanded state.

Figure 7A:
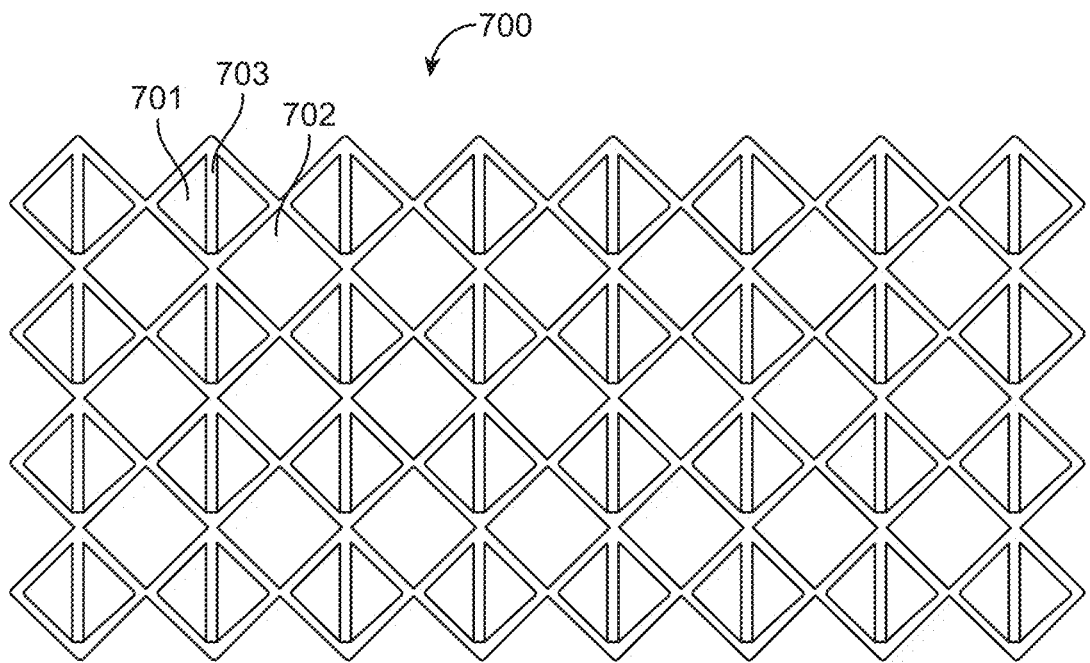
FIG. 7A is a two-dimensional depiction of an element having a ratcheting configuration.

FIGS. 7A-7F illustrate an embodiment of a stent element having a ratcheting configuration. While FIGS. 7A-7F depict cells with diamond configurations, cells may have any closed cell configuration. FIG. 7A is a two-dimensional depiction of an element having a ratcheting configuration.

Figure 7B:
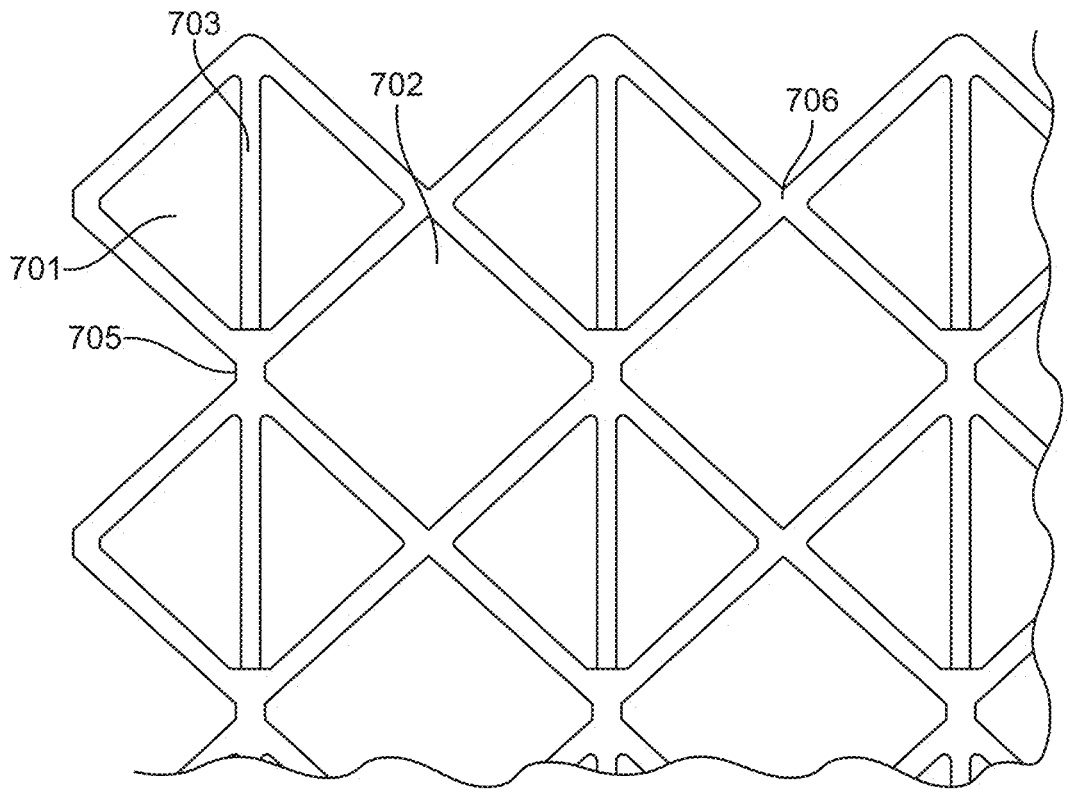
FIG. 7B is a magnified view of the cells in FIG. 7A.
Figure 7C:
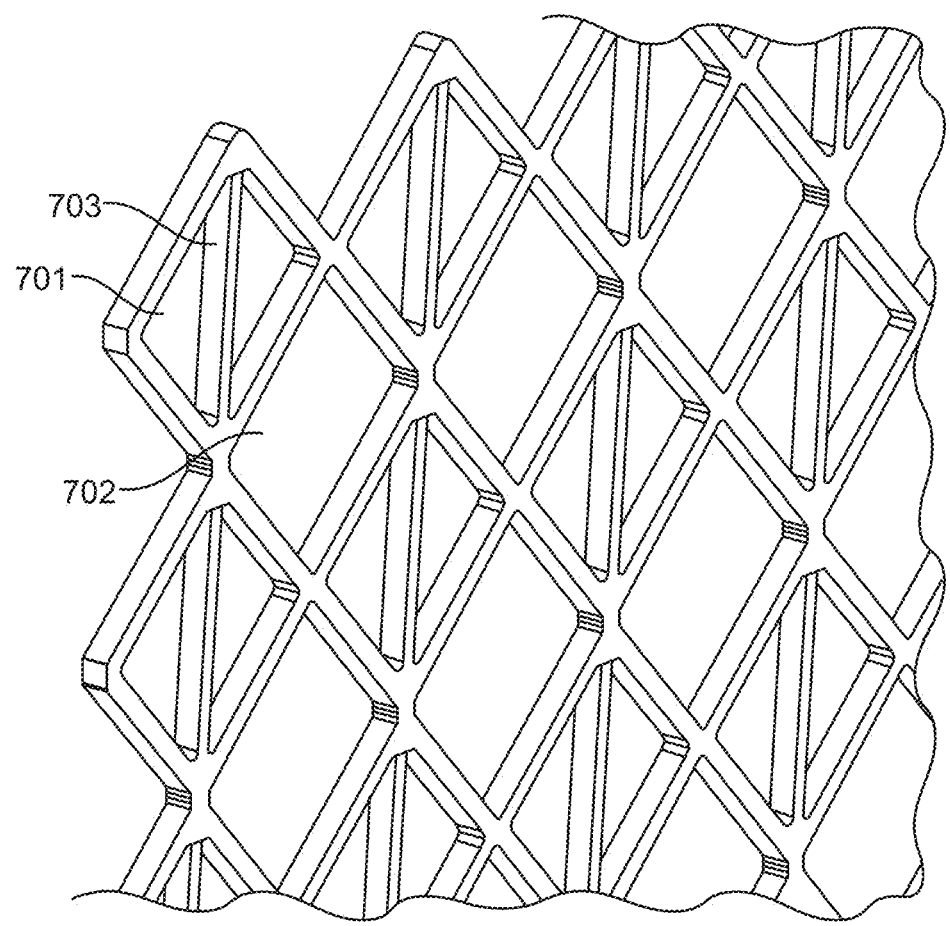
FIG. 7C is an isometric view of the cells in FIG. 7A.
Figure 7D:
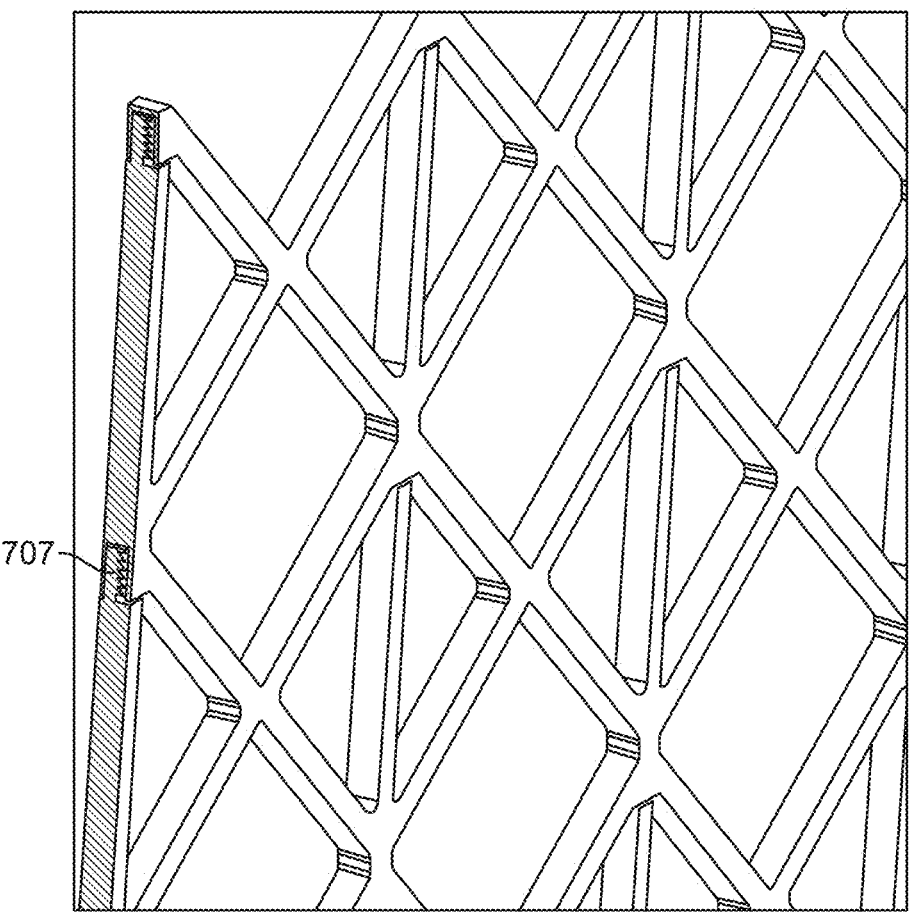
FIG. 7D is a cross-sectional view of the cells in FIG. 7C showing a ratchet.
Figure 7E:
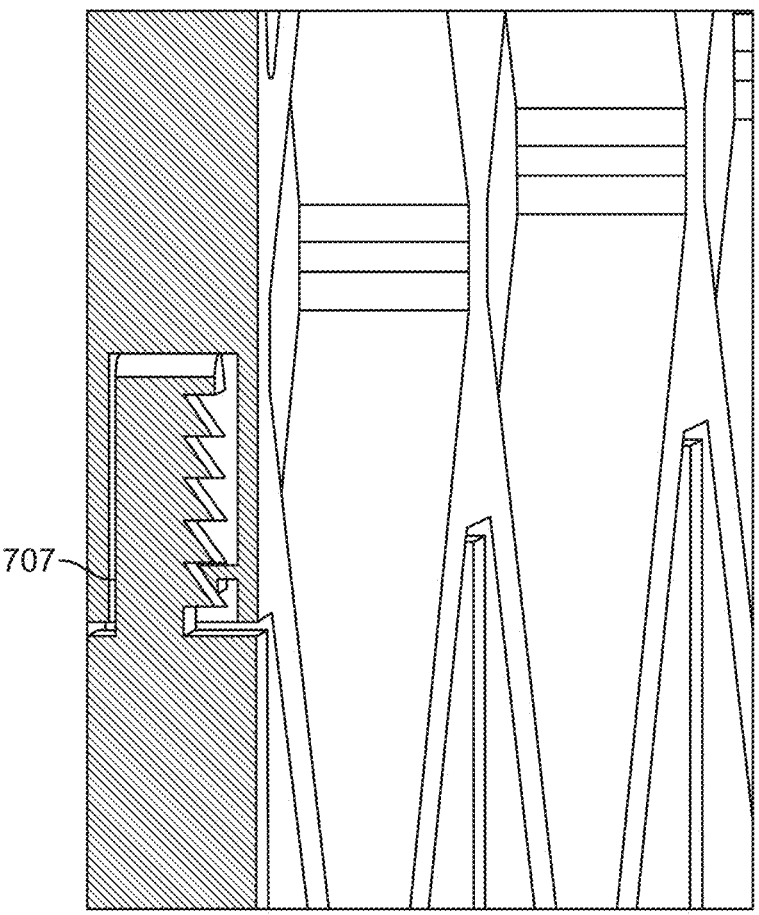
FIG. 7E is a magnified view of a ratchet in FIG. 7D.
Figure 7F:
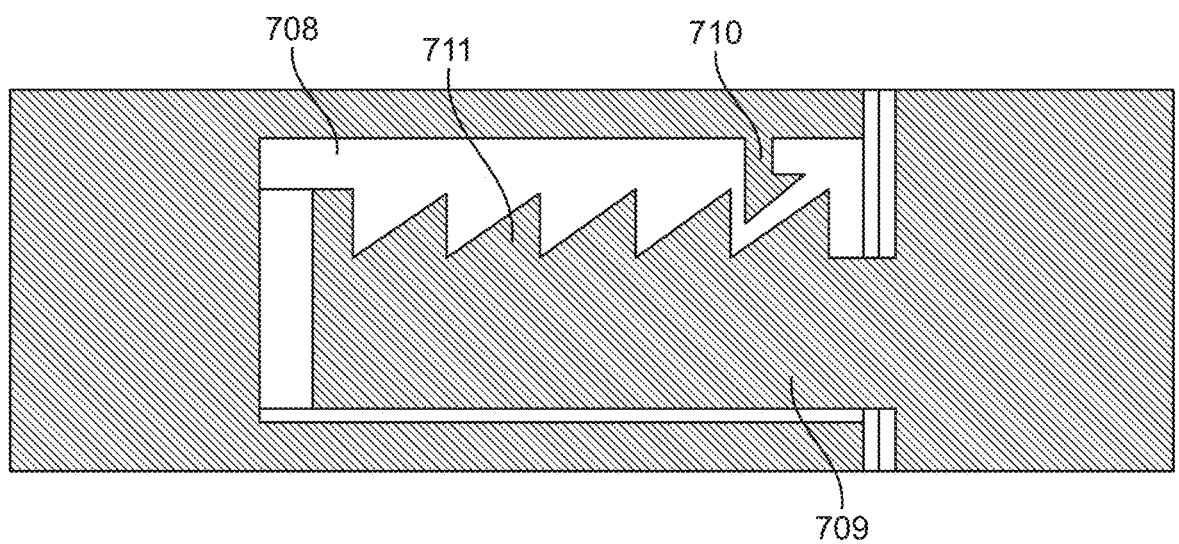
FIG. 7F is an alternative view of a ratchet in cross-section.

FIG. 7B is a magnified view of the cells in FIG. 7A. FIG. 7C is an isometric view of the cells in FIG. 7A. FIG. 7D is a cross-sectional view of the cells in FIG. 7C showing the ratchet 707. FIG. 7E is a magnified view of a ratchet 707 in FIG. 7D. FIG. 7F is an alternative view of a ratchet 707 in cross-section. A stent element with the cell structure of FIG. 7A would have a wrap orientation of left to right to form a cylinder. In this embodiment, element 700 comprises intermixed ratcheting cells 701 and non-ratcheting cells 702. Ratcheting cells 701 may be aligned in the longitudinal and/or the circumferential directions in a repeating pattern. Similarly, non-ratcheting cells 702 may be aligned in the longitudinal and/or the circumferential directions in a repeating pattern. Additionally or alternatively, non-ratcheting cells 702 and ratcheting cells 701 may be helically aligned in an alternating pattern. In an embodiment, non-ratcheting 702 and ratcheting cells 701 are circumferentially offset. Additionally, non-ratcheting cells 702 may be formed at a central location between four adjacent ratcheting cells 701. In an embodiment illustrated in FIGS. 7A-7F, ratcheting cells 701 may have the same or similar size as non-ratcheting cells 702. Alternatively, ratcheting cells 701 may be larger or smaller than non-ratcheting cells 702. Adjacent longitudinally aligned ratcheting cells 701 may be connected by longitudinal connecting struts 705. Adjacent circumferentially aligned ratcheting cells 701 may be connected by circumferential connecting struts 706. In an embodiment, longitudinal connecting struts 705 may have larger lengths or widths than circumferential connecting struts 706. Alternatively, longitudinal connecting struts 705 may have the same lengths or widths as circumferential connecting struts 706. Ratcheting cells 701 comprise longitudinally aligned ratcheting struts 703. Longitudinally aligned corners of ratcheting cells 701 and/or longitudinal connecting struts 705 may comprise cavities 708 to house linear racks 709 on ratcheting struts 703. Pawl 710 engages teeth 711 of linear rack 709. Element 700 may take a crimped form when mounted on an unexpanded balloon. Likewise, element 700 may take an expanded form when expanded by a balloon. Linear rack 707 moves in a longitudinal direction into cavity 708 (depicted as down to up in FIG. 7E and right to left in FIG. 7F) as the ratcheting element 700 moves from a crimped state to an expanded state. Ratchet 707 would thereby increase the radial strength of element 700.

Figure 8A:
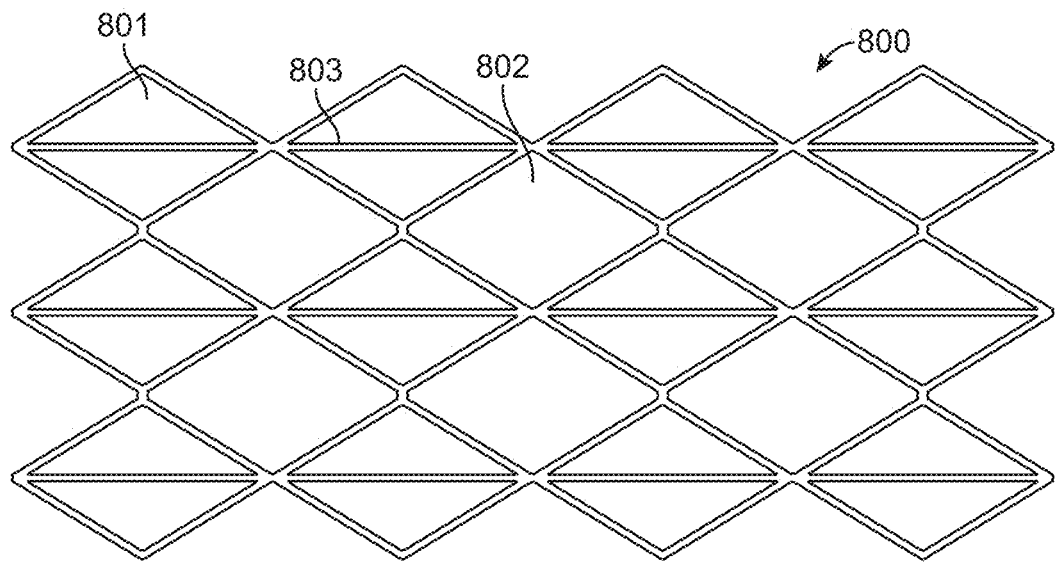
FIG. 8A is a two-dimensional depiction of an element having a bistable spring band configuration.
Figure 8B:
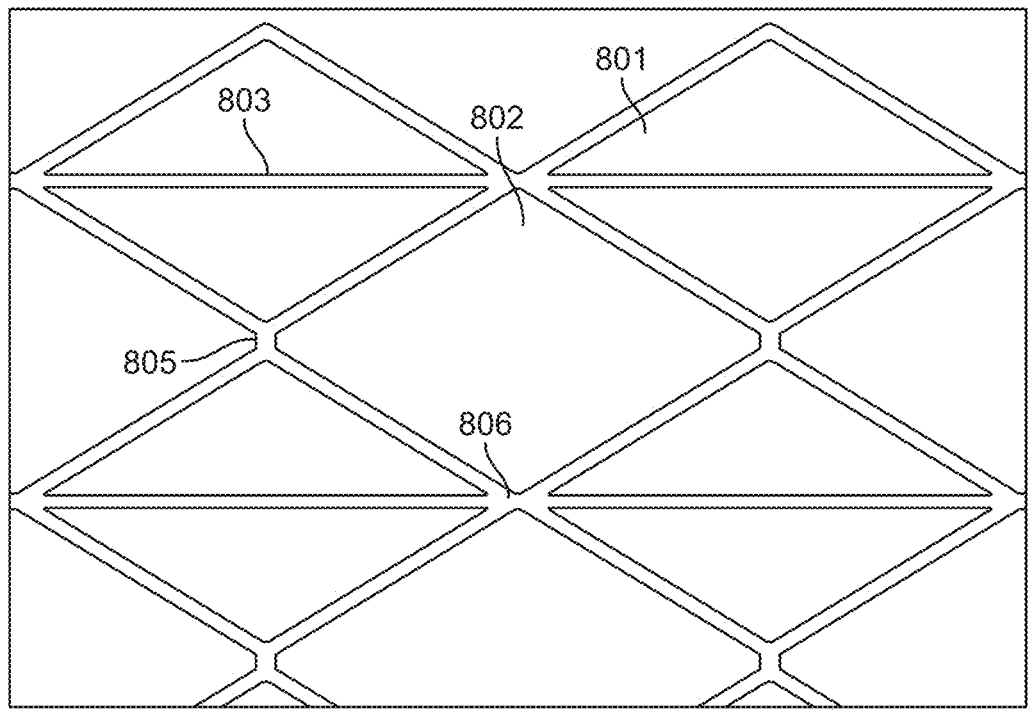
FIG. 8B is a magnified view of the cells in FIG. 8A.
Figure 8C:
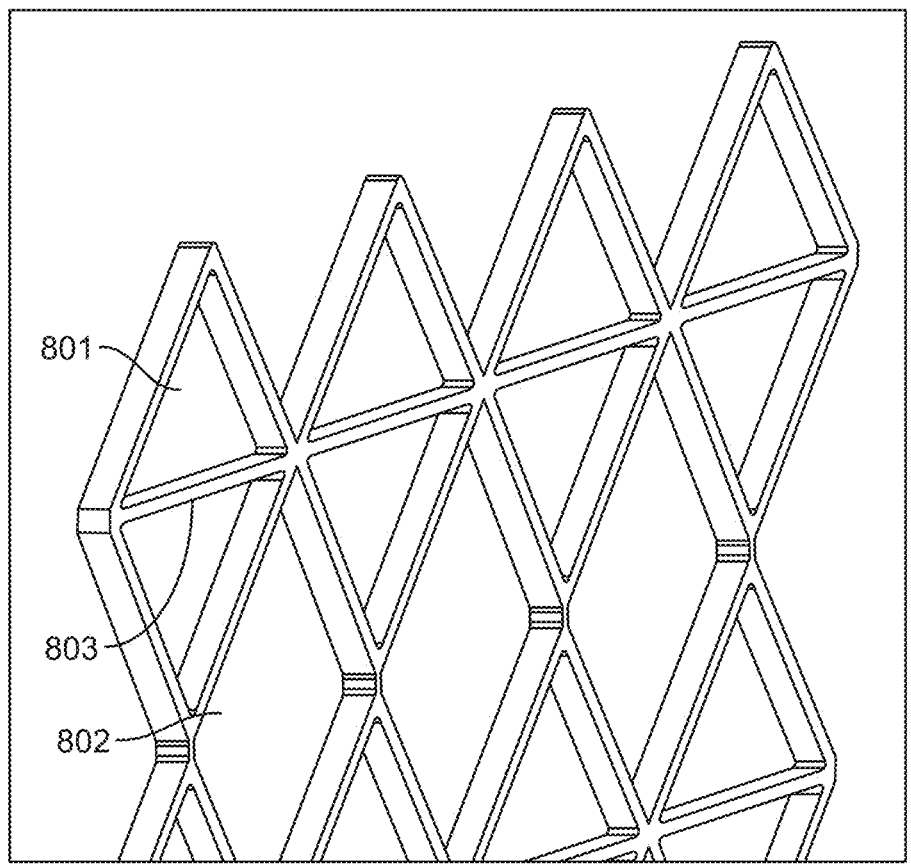
FIG. 8C is an isometric view of the cells in FIG. 8A.
Figure 8D:
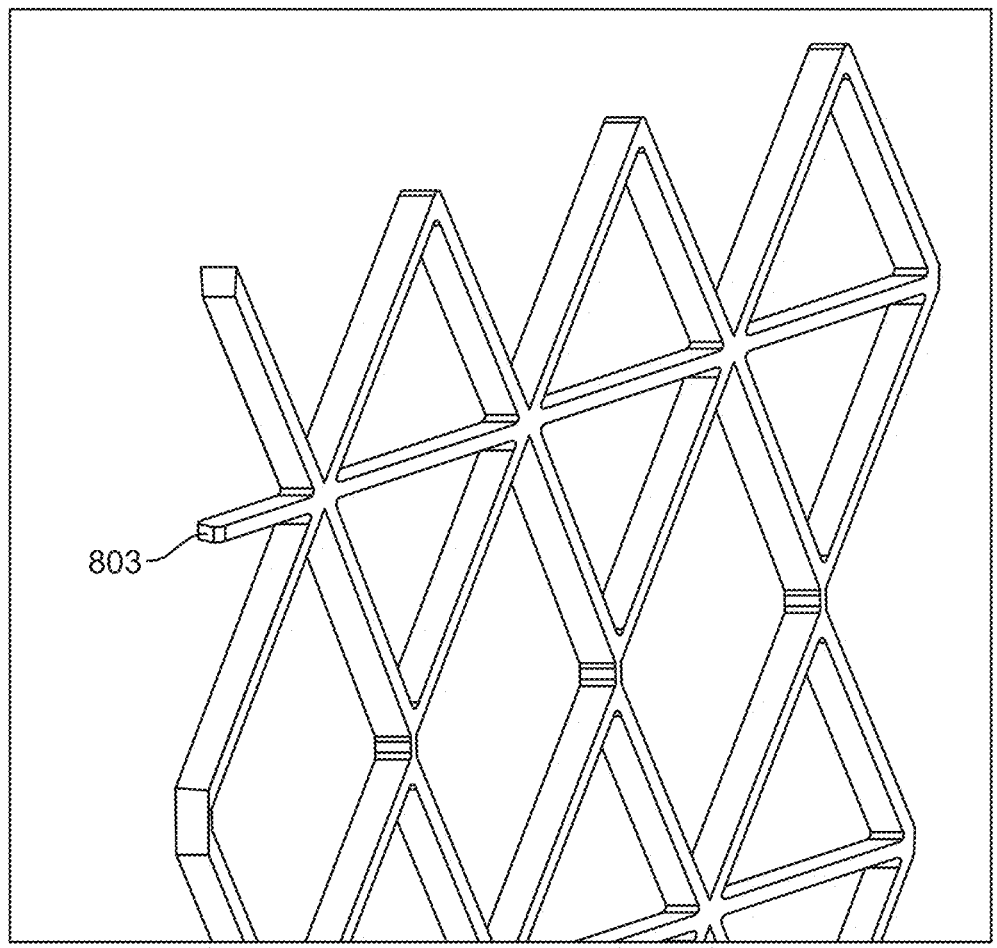
FIG. 8D is a cross-sectional view of the cells in FIG. 8C showing the curvature of bistable strut.
Figure 8E:
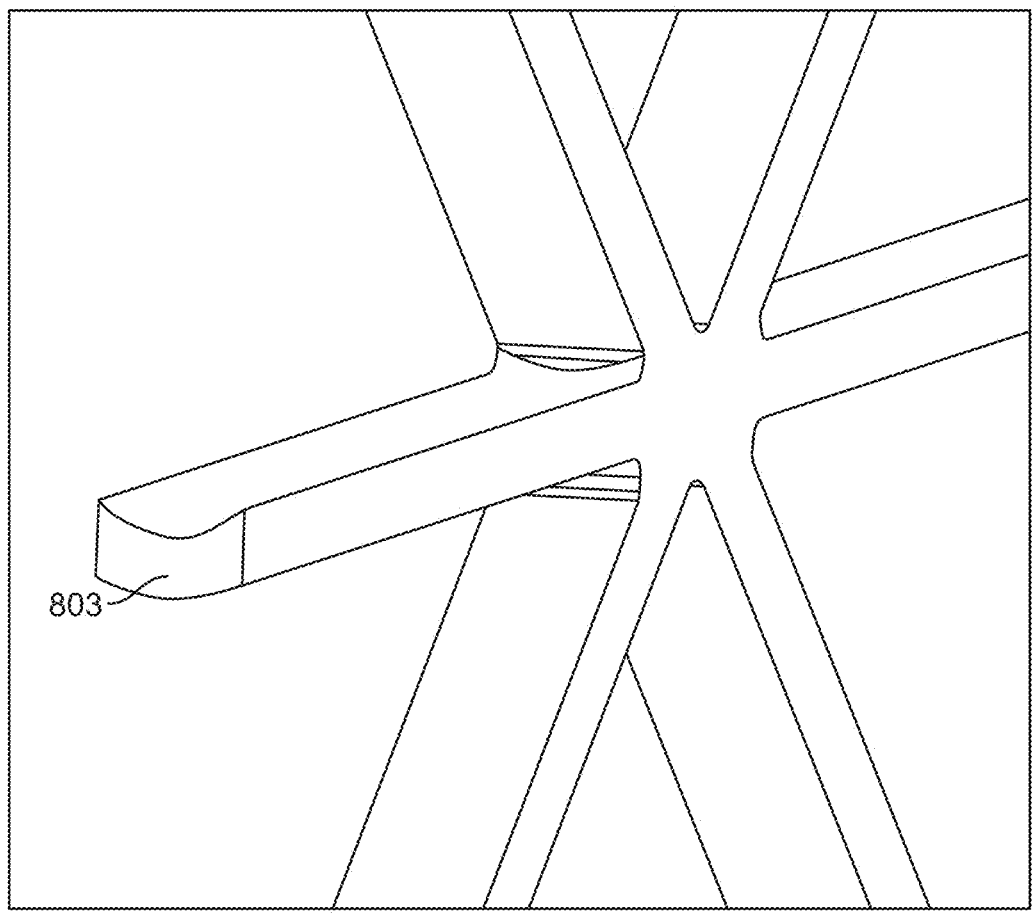
FIG. 8E is a magnified view of a bistable strut in FIG. 8D.
Figure 8F:
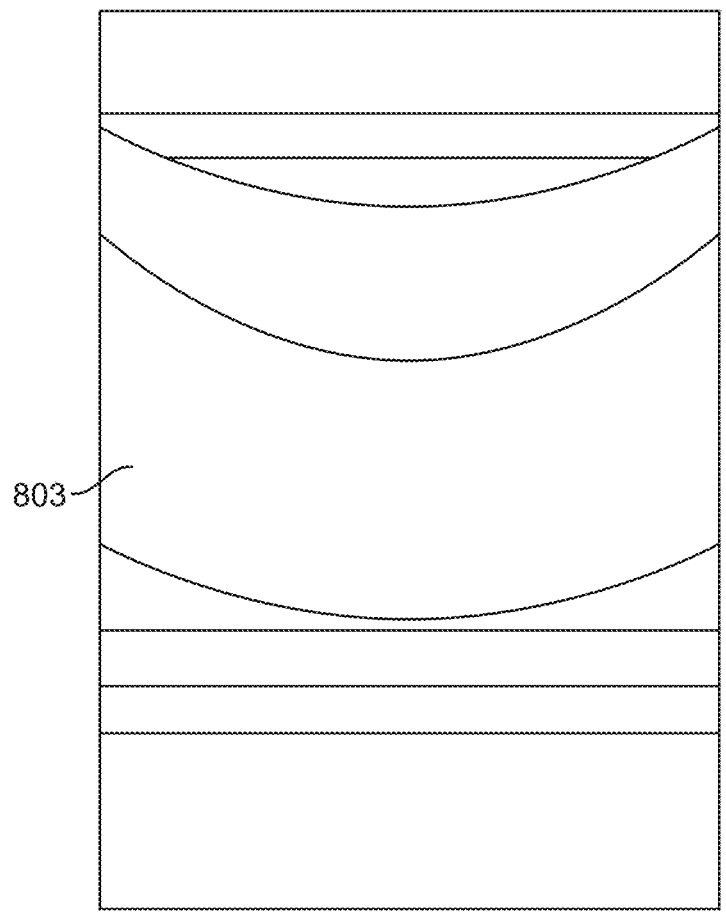
FIG. 8F is an alternative view of a bistable strut in cross-section.

FIGS. 8A-8F illustrate an embodiment of a stent element having a bistable spring band configuration. While FIGS. 8A-8F depict cells with diamond configurations, cells may have any closed cell configuration. FIG. 8A is a two-dimensional depiction of an element having a bistable spring band configuration. FIG. 8B is a magnified view of the cells in FIG. 8A. FIG. 8C is an isometric view of the cells in FIG. 8A. FIG. 8D is a cross-sectional view of the cells in FIG. 8C showing the curvature of bistable strut 803. FIG. 8E is a magnified view of a bistable strut 803 in FIG. 8D. FIG. 8F is an alternative view of a bistable strut 803 in cross-section. A stent element with the cell structure of FIG. 8A would have a wrap orientation of left to right to form a cylinder. In this embodiment, element 800 comprises intermixed bistable cells 801 and non-bistable cells 802. Bistable cells 801 may be aligned in the longitudinal and/or the circumferential directions in a repeating pattern. Similarly, non-bistable cells 802 may be aligned in the longitudinal and/or the circumferential directions in a repeating pattern. Additionally or alternatively, non-bistable cells 802 and bistable cells 801 may be helically aligned in an alternating pattern. In an embodiment, non-bistable 802 and bistable cells 801 are circumferentially offset. Additionally, non-bistable cells 802 may be formed at a central location between four adjacent bistable cells 801. In an embodiment illustrated in FIGS. 8A-8F, bistable cells 801 may have the same or similar size as non-bistable cells 802. Alternatively, bistable cells 1301 may be larger or smaller than non-bistable cells 802. Adjacent longitudinally aligned bistable cells 801 may be connected by longitudinal connecting struts 805. Adjacent circumferentially aligned bistable cells 801 may be connected by circumferential connecting struts 806. In an embodiment, longitudinal connecting struts 805 may have larger lengths or widths than circumferential connecting struts 806. Alternatively, longitudinal connecting struts 805 may have the same lengths or widths as circumferential connecting struts 806. Bistable cells 801 comprise circumferentially aligned bistable struts 803. Bistable struts 803 have a bistable spring band configuration. In an embodiment, bistable struts 803 have a concavo-convex shape. Bistable struts 803 may take a straight form or a bent form wherein the bistable strut 803 bends in the concave direction. Rigidity of the bistable strut 803 in the straight form increases raidial strength of the element 800. As depicted in FIGS. 8C-8F, the concave curve of bistable strut 803 is oriented in the longitudinal direction and would face a proximal or distal opening of the cylindrical element 800. Element 800 may take a crimped form when mounted on an unexpanded balloon. Likewise, element 800 may take an expanded form when expanded by a balloon. Bistable strut 803 would have a bent configuration in the crimped form. In the expanded state, the bistable strut would have a straight configuration.

Figure 9A:
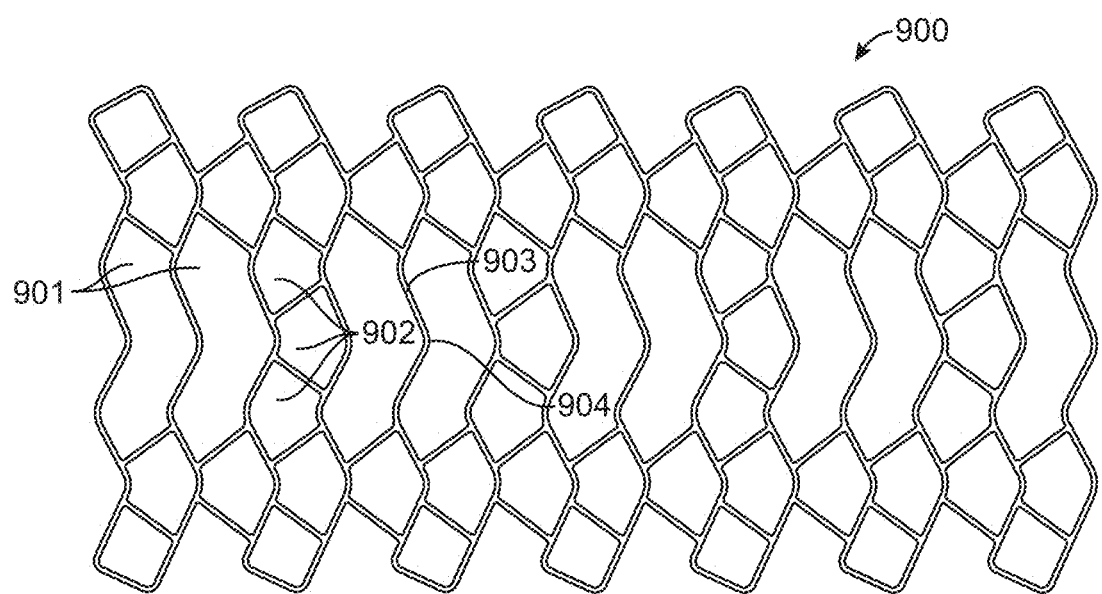
FIG. 9A is a two-dimensional depiction of an element having a pivoting configuration.
Figure 9B:
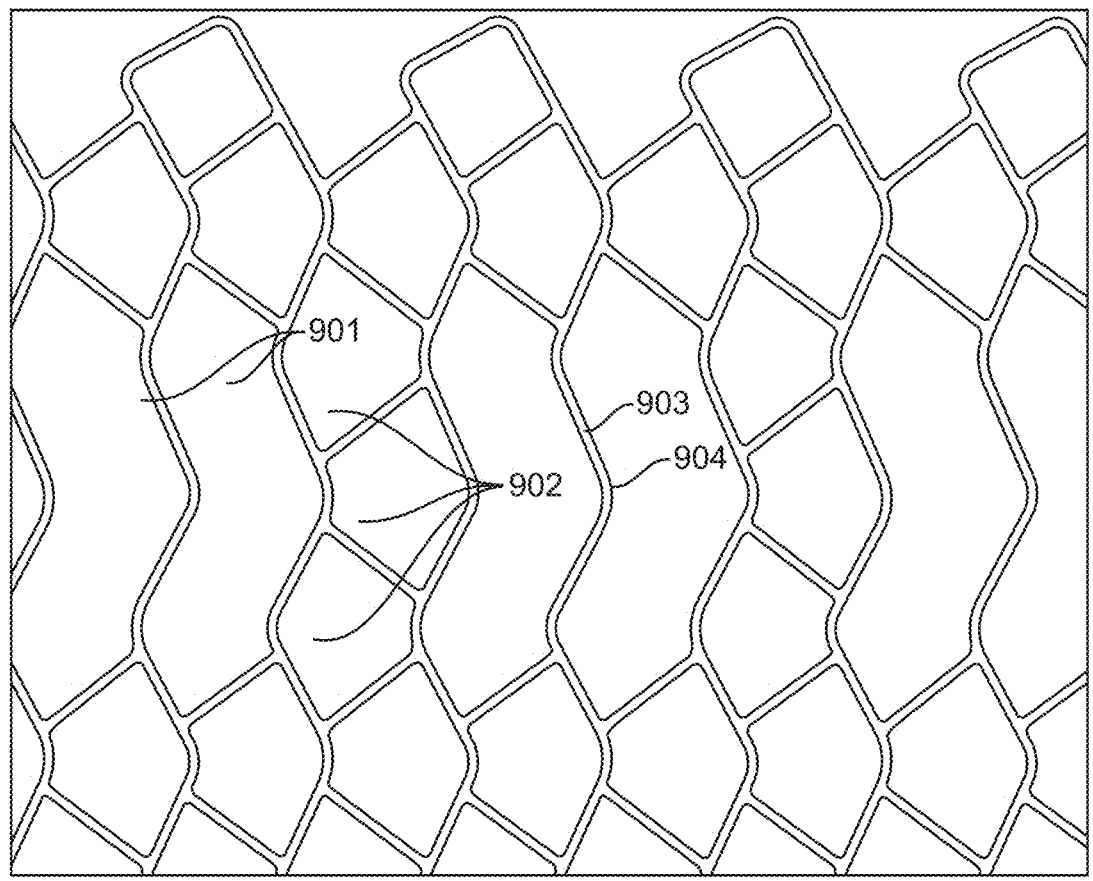
FIG. 9B is a magnified view of the cells in FIG. 9A.

FIGS. 9A-9B illustrate an embodiment of a stent element having a pivoting configuration. FIG. 9A is a two-dimensional depiction of an element having a pivoting configuration. FIG. 9B is a magnified view of the cells in FIG. 9A. A stent element with the cell structure of FIG. 9A would have a wrap orientation of left to right to form a cylinder. In this embodiment, element 900 comprises an alternating sequence of two larger cells 901 and a set of smaller cells 902. The two larger cells 901 allow bending of the free moving pivoting strut 903 separating the two larger cells 901. Element 900 may take a crimped form when mounted on an unexpanded balloon. Likewise, element 900 may take an expanded form when expanded by a balloon. FIGS. 9A-9B depict the pivoting strut 903 in an unstable, less rigid configuration present when the element 900 is in a crimped state. When expanded, the apex 904 of the pivoting strut 903 would shift from the right to the left (based on the orientation in FIG. 9A-9B), thereby increasing the rigidity of the pivoting strut9 and increasing the radial strength of the element 900.

The device described herein may include incorporation of a therapeutic drug intended to prevent or attenuate pathologic consequences of intraluminal intervention such as inflammation, cell dysfunction, cell activation, cell proliferation, neointimal formation, thickening, late atherosclerotic change and/or thrombosis. Any suitable therapeutic agent (or "drug") may be incorporated into, coated on, or otherwise attached to the stent, in various embodiments. Examples of such therapeutic agents include, but are not limited to, antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, anti-neoplastics, agents that promote endothelial cell recovery, matrix metalloproteinase inhibitors, anti-metabolites, antiallergic substances, viral vectors, nucleic acids, monoclonal antibodies, inhibitors of tyrosine kinase, antisense compounds, oligonucleotides, cell permeation enhancers, hypoglycemic agents, hypolipidemic agents, proteins, nucleic acids, agents useful for erythropoiesis stimulation, angiogenesis agents, anti-ulcer/anti-reflux agents, and anti-nauseants/anti-emetics, PPAR alpha agonists such as fenofibrate, PPAR-gamma agonists selected such as rosiglitazaone and pioglitazone, sodium heparin, LMW heparins, heparoids, hirudin, argatroban, forskolin, vapriprost, prostacyclin and prostacylin analogues, dextran, D-phe-pro-arg-chloromethylketone (synthetic anti-thrombin), glycoprotein IIb/IIIa (platelet membrane receptor antagonist antibody), recombinant hirudin, thrombin inhibitors, indomethacin, phenyl salicylate, beta-estradiol, vinblastine, ABT-627 (astrasentan), testosterone, progesterone, paclitaxel, methotrexate, fotemusine, RPR-101511A, cyclosporine A, vincristine, carvediol, vindesine, dipyridamole, methotrexate, folic acid, thrombospondin mimetics, estradiol, dexamethasone, metrizamide, iopamidol, iohexol, iopromide, iobitridol, iomeprol, iopentol, ioversol, ioxilan, iodixanol, and iotrolan, antisense compounds, inhibitors of smooth muscle cell proliferation, lipid-lowering agents, radiopaque agents, antineoplastics, HMG CoA reductase inhibitors such as lovastatin, atorvastatin, simvastatin, pravastatin, cerivastatin and fluvastatin, and combinations thereof.

Examples of antithrombotics, anticoagulants, antiplatelet agents, and thrombolytics include, but are not limited to, sodium heparin, unfractionated heparin, low molecular weight heparins, such as dalteparin, enoxaparin, nadroparin, reviparin, ardoparin and certaparin, heparinoids, hirudin, argatroban, forskolin, vapriprost, prostacyclin and prostacylin analogues, dextran, D-phe-pro-arg-chloromethylketone (synthetic antithrombin), dipyridamole, glycoprotein IIb/IIIa (platelet membrane receptor antagonist antibody), recombinant hirudin, and thrombin inhibitors such as bivalirudin, thrombin inhibitors, and thrombolytic agents, such as urokinase, recombinant urokinase, pro-urokinase, tissue plasminogen activator, ateplase and tenecteplase.

Examples of cytostatic or antiproliferative agents include, but are not limited to, rapamycin and its analogs, including everolimus, zotarolimus, tacrolimus, novolimus, and pimecrolimus, angiopeptin, angiotensin converting enzyme inhibitors, such as captopril, cilazapril or lisinopril, calcium channel blockers, such as nifedipine, amlodipine, cilnidipine, lercanidipine, benidipine, trifluperazine, diltiazem and verapamil, fibroblast growth factor antagonists, fish oil (omega 3-fatty acid), histamine antagonists, lovastatin, topoisomerase inhibitors, such as etoposide and topotecan, as well as antiestrogens such as tamoxifen.

Examples of anti-inflammatory agents include, but are not limited to, colchicine and glucocorticoids, such as betamethasone, cortisone, dexamethasone, budesonide, prednisolone, methylprednisolone and hydrocortisone. Non-steroidal anti-inflammatory agents include, but are not limited to, flurbiprofen, ibuprofen, ketoprofen, fenoprofen, naproxen, diclofenac, diflunisal, acetominophen, indomethacin, sulindac, etodolac, diclofenac, ketorolac, meclofenamic acid, piroxicam and phenylbutazone.

Examples of antineoplastic agents include, but are not limited to, alkylating agents including altretamine, bendamucine, carboplatin, carmustine, cisplatin, cyclophosphamide, fotemustine, ifosfamide, lomustine, nimustine, prednimustine, and treosulfin, antimitotics, including vincristine, vinblastine, paclitaxel, docetaxel, antimetabolites including methotrexate, mercaptopurine, pentostatin, trimetrexate, gemcitabine, azathioprine, and fluorouracil, antibiotics, such as doxorubicin hydrochloride and mitomycin, and agents that promote endothelial cell recovery such as estradiol.

Antiallergic agents include, but are not limited to, permirolast potassium nitroprusside, phosphodiesterase inhibitors, prostaglandin inhibitors, suramin, serotonin blockers, steroids, thioprotease inhibitors, triazolopyrimidine, and nitric oxide.

The beneficial agent may include a solvent. The solvent may be any single solvent or a combination of solvents. For purpose of illustration and not limitation, examples of suitable solvents include water, aliphatic hydrocarbons, aromatic hydrocarbons, alcohols, ketones, dimethyl sulfoxide, tetrahydrofuran, dihydrofuran, dimethylacetamide, acetates, and combinations thereof.

Stents may be manufactured using an additive or a subtractive. In any of the described embodiments, stents or stent elements may be manufactured as a sheet and wrapped into cylindrical form. Alternatively, stents or stent elements may be manufactured in cylindrical form using an additive manufacturing process. In an embodiment, stents maybe formed by extruding a material into a cylindrical tubing. In some embodiments, a longer stent element, may be formed during the manufacturing process and then cut into smaller stent elements/elements to provide a multi-element stent. In an embodiment, stent tubing may be laser cut with a pattern to form a stent element.

Figure 10:
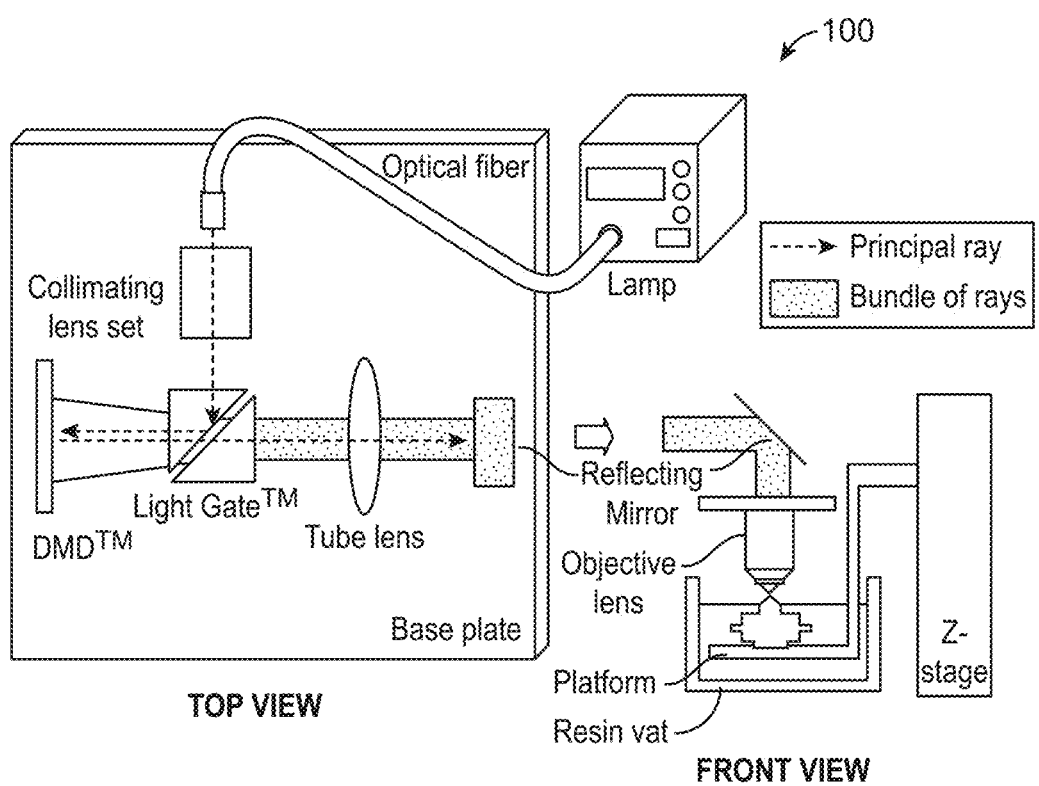
FIG. 10 is a schematic diagram of a micro-stereolithograph used to create a stent, according to one embodiment.

Referring now to FIG. 10, in one embodiment, stents may be manufactured using a micro-stereolithography system 100 (or "3D printing system"). Several examples of currently available systems that might be used in various embodiments include, but are not limited to: MakiBox A6, Makible Limited, Hong Kong; CubeX, 3D Systems, Inc., Circle Rock Hill, SC; and 3D-Bioplotter, (EnvisionTEC GmbH, Gladbeck, Germany).

The micro-stereolithography system may include an illuminator, a dynamic pattern generator, an image-former and a Z-stage. The illuminator may include a light source, a filter, an electric shutter, a collimating lens and a reflecting mirror that projects a uniformly intense light on a digital mirror device (DMD), which generates a dynamic mask. FIG. 10 shows some of these components of one embodiment of the micro-stereolithography system 100, including a DMD board, Z-stage, lamp, platform, resin vat and an objective lens. The details of 3D printing/micro-stereolithography systems and other additive manufacturing systems will not be described here, since they are well known in the art. However, according to various embodiments, any additive manufacturing system or process, whether currently known or hereafter developed, may potentially be used to fabricate stents within the scope of the present invention. In other words, the scope of the invention is not limited to any particular additive manufacturing system or process.

In one embodiment, the system 100 may be configured to fabricate stents using dynamic mask projection micro-stereolithography. In one embodiment, the fabrication method may include first producing 3D microstructural scaffolds by slicing a 3D model with a computer program and solidifying and stacking images layer by layer in the system. In one embodiment, the reflecting mirror of the system is used to project a uniformly intense light on the DMD, which generates a dynamic mask. The dynamic pattern generator creates an image of the sliced section of the fabrication model by producing a black-and-white region similar to the mask. Finally, to stack the images, a resolution Z-stage moves up and down to refresh the resin surface for the next curing. The Z-stage build subsystem, in one embodiment, has a resolution of about 100 nm and includes a platform for attaching a substrate, a vat for containing the polymer liquid solution, and a hot plate for controlling the temperature of the solution. The Z-stage makes a new solution surface with the desired layer thickness by moving downward deeply, moving upward to the predetermined position, and then waiting for a certain time for the solution to be evenly distributed.

Because the device is comprised of fully bioresorbable material, it slowly begins to weaken and dissolve soon after being subjected to a warm, biologically active environment. The device is designed such that its rigidity is slowly attenuated as its structural polymer is unlinked and metabolized. As the device weakens, its effect on the arterial wall is slowly released. Eventually, the device ceases to exert any radial effect on its host artery thus completely removing any pathologic stimuli for neointimal hyperplasia formation, ongoing thickening and maladaptation. The lack of continuous stimulation by an intravascular foreign body allows the vessel to re-enter a quiescent, patent state until such time that further plaque might be generated by its host.

Figure 11A:
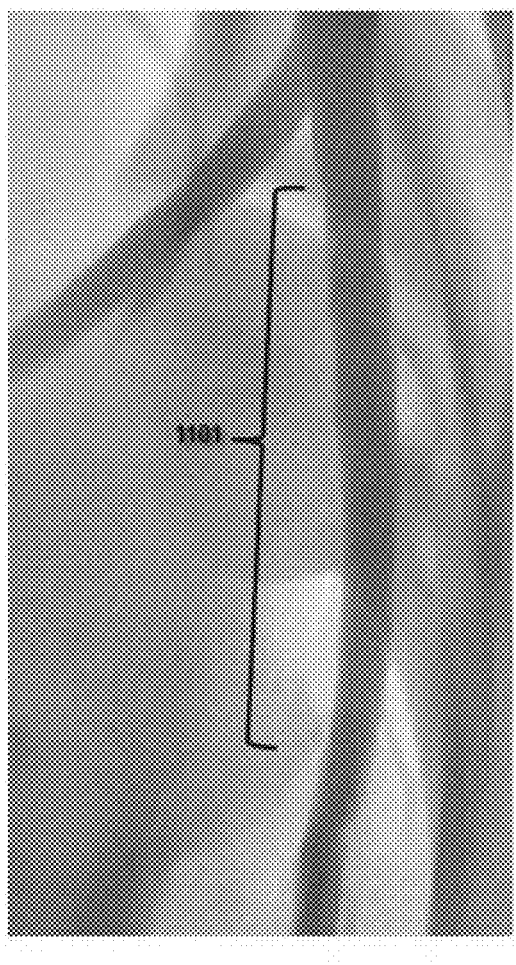
FIG. 11A shows an angiographic image of a porcine iliofemoral artery treated with a device described herein.
Figure 11B:
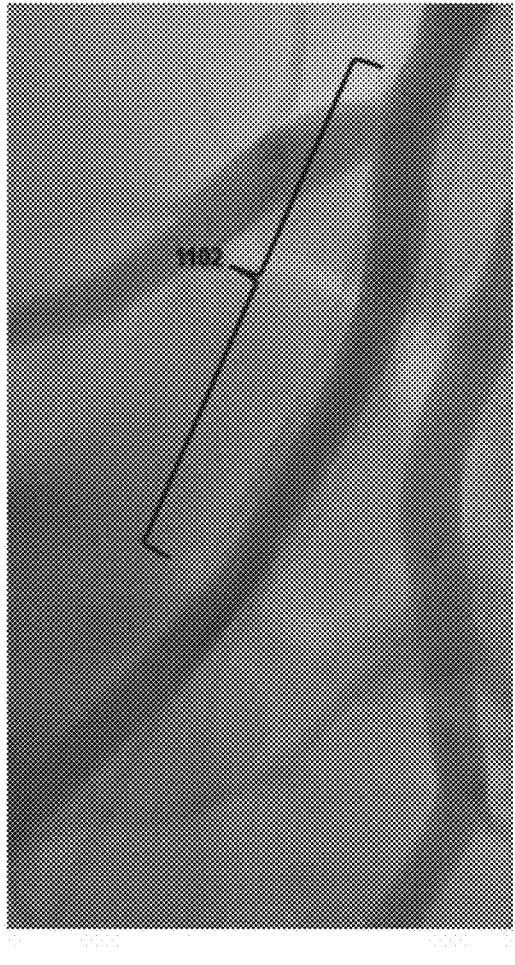
FIG. 11B shows an angiographic image of an iliofemoral artery of the same pig in FIG. 11A with a self-expanding nitinol stent.

FIG. 11A shows an angiographic image of a porcine iliofemoral artery treated with a device described herein at 1101 after one year. FIG. 11B shows an angiographic image of an iliofemoral artery of the same pig treated with a self-expanding nitinol stent at 1102 after one year. The artery containing the self-expanding stent shows clear neointimal hyperplasia while the artery in FIG. 11A does not.

Figure 12:
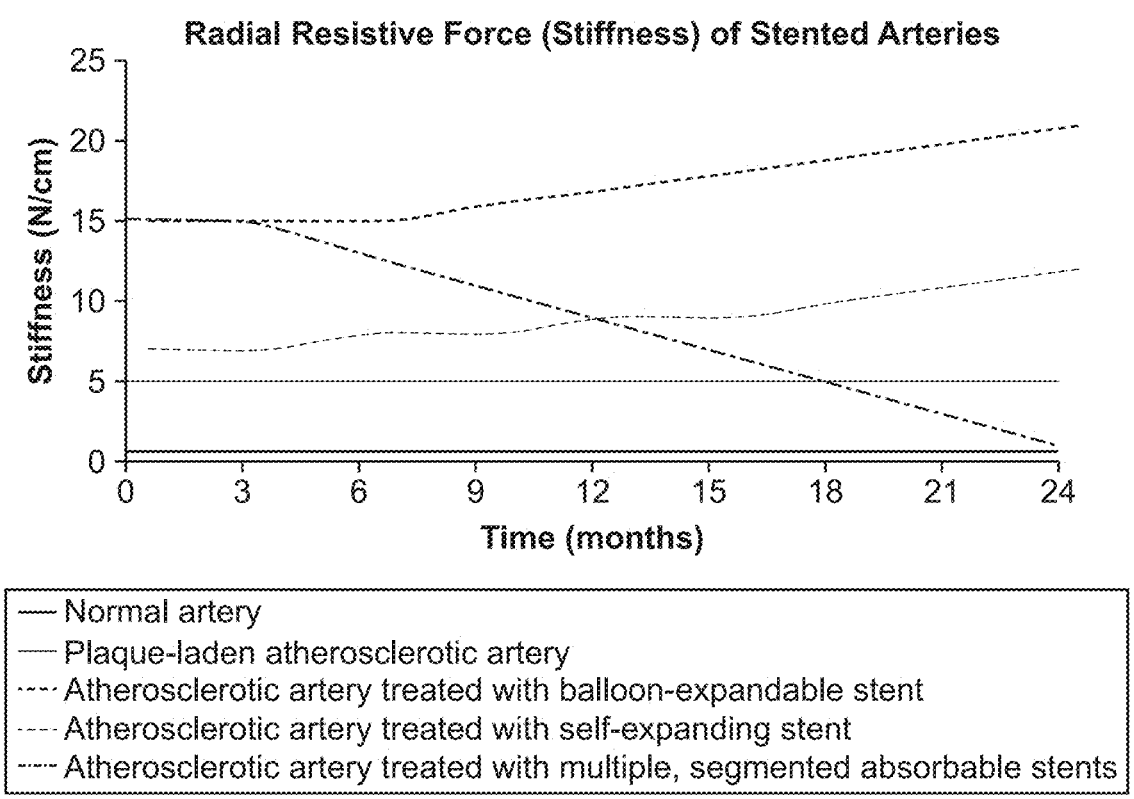
FIG. 12 shows the radial resistive force of stented arteries over time.

FIG. 12 shows the radial resistive force of stented arteries over time. A normal healthy artery has a radial resistive force of less than 1 N/cm. A plaque-laden atherosclerotic artery has a radial resistive force of approximately 5 N/cm. An atherosclerotic artery treated with a traditional metal balloon-expandable stent has an initial radial resistive force of approximately 15 N/cm. The artery containing the metal stent becomes more rigid over time. An atherosclerotic artery treated with a self-expanding stent may have an initial radial resistive force of approximately 7 N/cm. The artery containing self-expanding stent will similarly become more rigid over time.

An atherosclerotic artery treated with the device described herein has an initial radial resistive force similar to that of an artery treated with a metal balloon expandable stent, approximately 15 N/cm. In other embodiments, the bioresorbable stent may have cause an initial radial resistive force in the range of 10 to 20 N/cm. As the bioresorbable stent dissolves it slowly becomes more flexible allowing adaptation and remodeling of the artery such that the artery's elasticity is restored. In an embodiment, the bioresorbable stent dissolves over a period of approximately two years causing the radial rigidity of the stent to decrease over the same period. In other embodiments, the bioresorbable stent may dissolve over a period in the range of 1.5 to 3 years. The radial resistive force of an atherosclerotic artery treated with the bioresorbable stent decreases over time to a stiffness approaching that of a healthy artery, less than 1 N/cm. The thickness of the stent, cell shape, polymer materials, and/or processing or treatment of the polymers may be configured to give a specific dissolution rate and to provide the desired decrease in radial rigidity of the vessel over time.

Although particular embodiments have been shown and described, they are not intended to limit the invention. Various changes and modifications may be made to any of the embodiments, without departing from the spirit and scope of the invention. The invention is intended to cover alternatives, modifications, and equivalents.

What is claimed is:

1. A method for maintaining or enhancing blood flow through a blood vessel, the method comprising:
advancing a balloon catheter into the blood vessel;
expanding a balloon on the balloon catheter to expand multiple, bioresorbable polymer, vascular stent elements disposed on the balloon to contact an inner wall of the blood vessel, wherein the stent elements are spaced such that the stent elements do not touch one another, wherein the stent elements are formed from a bioresorbable structural polymer material;
deflating the balloon, while leaving the vascular stent elements in place in the blood vessel; and
removing the balloon catheter from the blood vessel;
wherein the stent elements comprise diamond shaped closed cells;
wherein a radial rigidity of the stent elements is configured to decrease after implantation in a vessel as the structural polymer material is absorbed;
wherein a thickness of the stent elements, a shape of the closed cells, a cell pattern of the stent elements, and the structural polymer material are configured to provide an initial radial rigidity to the vessel upon implantation of approximately 15 N/cm or more;
wherein the stent elements are configured to dissolve over a period of approximately 2 years after implantation such that the radial rigidity of the stent elements is slowly attenuated as its structural polymer material is unlinked and metabolized such that the stent elements slowly become more flexible causing adaptation and remodeling of the vessel and restoration of the vessel's elasticity;
wherein the stent elements are configured to provide a decrease in the radial rigidity of the vessel over a period of approximately 2 years to a radial rigidity of less than 1 N/cm, and wherein the thickness of the stent elements, the shape of the closed cells, the cell pattern of the stent elements, the structural polymer material, and a treatment of the structural polymer material are configured to provide the decrease in radial rigidity of the vessel over time; wherein the stents elements have a thickness of approximately 115 to 145 microns; and wherein the stent elements are formed by struts having a width of approximately 95 to 125 microns.

2. The method of claim 1, wherein the closed cells comprise a first set of closed cells and a second set of closed cells.

3. The method of claim 2, wherein the first set of closed cells have a repeating adjacent longitudinally aligned pattern and a repeating adjacent circumferentially aligned pattern, wherein the second set of closed cells have a repeating adjacent longitudinally aligned pattern and a repeating adjacent circumferentially aligned pattern, wherein the first set of closed cells and the second set of closed cells are circumferentially offset, and wherein the first set of closed cells and the second set of closed cells have a helically aligned repeating adjacent alternating pattern.

4. The method of claim 3, wherein the first set of closed cells and the second set of closed cells have the same shape and size.

5. The method of claim 3, wherein the first set of closed cells and the second set of closed cells have a different shape and or size.

* * * * *